(12) United States Patent
Rubbert et al.

(10) Patent No.: US 6,632,089 B2
(45) Date of Patent: Oct. 14, 2003

(54) ORTHODONTIC TREATMENT PLANNING WITH USER-SPECIFIED SIMULATION OF TOOTH MOVEMENT

(75) Inventors: Rüdger Rubbert, Berlin (DE); Thomas Weise, Berlin (DE); Rohit Sachdeva, Plano, TX (US); Hans Imgrund, Berlin (DE); Peer Sporbert, Berlin (DE); Mario Leichner, Hohen Neuendorf (DE); Jens Troeger, Berlin (DE); Dimitrij Kouzian, Berlin (DE); Stephan Maetzel, Berlin (DE)

(73) Assignee: OraMetrix, Inc., Dallas, TX (US)

( * ) Notice: Subject to any disclaimer, the term of this patent is extended or adjusted under 35 U.S.C. 154(b) by 187 days.

(21) Appl. No.: 09/834,412

(22) Filed: Apr. 13, 2001

(65) Prior Publication Data

US 2002/0010568 A1 Jan. 24, 2002

Related U.S. Application Data

(63) Continuation-in-part of application No. 09/560,640, filed on Apr. 28, 2000, which is a continuation-in-part of application No. 09/451,609, filed on Nov. 30, 1999, now Pat. No. 6,250,918.

(51) Int. Cl.[7] .................................................. A61C 3/00
(52) U.S. Cl. ........................................................ 433/24
(58) Field of Search .............................. 433/24, 25, 72, 433/213; 700/98

(56) References Cited

U.S. PATENT DOCUMENTS

| 5,011,405 | A | 4/1991 | Lemchen ..................... 433/24 |
| 5,338,198 | A | 8/1994 | Wu et al. .................... 433/213 |
| 5,447,432 | A | 9/1995 | Andreiko et al. ............. 433/24 |
| 5,879,158 | A | 3/1999 | Doyle et al. ................. 433/24 |
| 5,975,893 | A | 11/1999 | Chishti et al. ................. 433/6 |
| 6,227,850 | B1 | 5/2001 | Chishti et al. ................ 433/24 |
| 6,227,851 | B1 | 5/2001 | Chishti et al. ................ 433/24 |
| 6,299,440 | B1 | 10/2001 | Phan et al. ................... 433/24 |
| 6,318,994 | B1 | 11/2001 | Chishti et al. ................ 433/24 |
| 6,334,853 | B1 | 1/2002 | Kopelman et al. .......... 600/590 |
| 6,371,761 | B1 | 4/2002 | Cheang et al. ............... 433/24 |
| 6,386,878 | B1 | 5/2002 | Pavlovskaia et al. ....... 433/215 |
| 2002/0025503 | A1 | 2/2002 | Chapoulaud et al. ......... 433/24 |
| 2002/0028417 | A1 | 3/2002 | Chapoulaud et al. ......... 433/24 |

FOREIGN PATENT DOCUMENTS

EP           0 250 993         *   6/1987

* cited by examiner

Primary Examiner—Todd E. Manahan
(74) Attorney, Agent, or Firm—McDonnell Boehnen Hulbert & Berghoff

(57) ABSTRACT

An interactive, software-based treatment planning method to correct a malocclusion is described. The method can be performed on an orthodontic workstation in a clinic or at a remote location such as a lab or precision appliance manufacturing center. The workstation stores a virtual three-dimensional model of the dentition of a patient and patient records. The virtual model is manipulated by the user to define a target situation for the patient, including a target archform and individual tooth positions in the archform. Parameters for an orthodontic appliance, such as the location of orthodontic brackets and resulting shape of an orthodontic archwire, are obtained from the simulation of tooth movement to the target situation and the placement position of virtual brackets. The treatment planning can also be executed remotely by a precision appliance service center having access to the virtual model of the dentition. In the latter situation, the proposed treatment plan is sent to the clinic for review, and modification or approval by the orthodontist. The method is suitable for other orthodontic appliance systems, including removable appliances such as transparent aligning trays.

45 Claims, 28 Drawing Sheets

308 302

310

308
310

312

ORTHODONTIC TREATMENT PLANNING WITH USER-SPECIFIED SIMULATION OF TOOTH MOVEMENT

CROSS-REFERENCE TO RELATED APPLICATIONS

This application is a continuation-in-part application of the following pending U.S. patent applications:

Ser. No. 09/560,640 filed Apr. 28, 2000 pending, which is a continuation in part of Ser. No. 09/451,609 filed Nov. 30, 1999 now U.S. Pat. No. 6,250,918. The entire contents of each of the above-reference patent applications is incorporated by reference herein.

NOTICE REGARDING COPYRIGHT

A portion of the disclosure of this patent document contains material which is subject to copyright protection. The copyright owner has no objection to the facsimile reproduction by anyone of the patent disclosure, at it appears in the Patent and Trademark Office files or records, but otherwise reserves all copyright rights whatsoever.

BACKGROUND OF THE INVENTION

A. Field of the Invention

This invention relates generally to the field of computer-interactive methods for diagnosis, care and treatment planning, therapeutics and treatment monitoring in the medical arena, including orthodontics. The invention also relates to real-time computer-interactive communication between a medical practitioner and his or her patient regarding diagnosis, care and treatment planning, therapeutics and treatment monitoring, and between a medical practitioner and a remotely located entities regarding these matters.

In the illustrated embodiment, the invention relates to a computerized and interactive method of planning orthodontic treatment for a patient suffering from a malocclusion. In the method, the patient's teeth are represented in a computer as three-dimensional virtual objects. The orthodontist may simulate various types of tooth movement and appliances, analyze the simulation, and thereby explore possible treatment options and appliance designs, prior to initiating treatment.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. An the patient has no choice and does not know the treatment time could be significantly reduced if proper planning was done.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give moe predictablity, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

The art has lacked an effective, computer-based interactive orthodontic treatment planning system that provides the necessary tools to allow the orthodontist to quickly and efficiently design a treatment plan for a patient. The art has also lacked a treatment planning system in which the orthodontist-derived parameters for the treatment can be translated into a design of an orthodontic appliance in real time, while the patient is in the chair. Real-time appliance design as described herein also allows for real-time communication of the treatment plan or appliance design to occur with the patient, or transmitted over a communications link and shared with a colleague or remote appliance manufacturing facility. Alternatively, the treatment planning can be performed remotely and a digital treatment plan sent to the orthodontist for review, interactive modification, or approval.

SUMMARY OF THE INVENTION

In a first aspect of the invention, apparatus for treatment planning for an orthodontic patient is provided. The apparatus can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition and develop and specify a target or desired stage. A shortest direct path of tooth movement to the target stage can also be determined. Further, the apparatus provides for simulation of tooth movement between current and target stages.

In its broader aspects, the apparatus comprises a workstation having a processing unit and a display, and a memory storing a virtual, complete three-dimensional model representing the dentition of a patient. The virtual three-dimensional model can be obtained from one of several possible sources; in the preferred embodiment it is arrived at from a scanning of the dentition. The apparatus further includes software executable by the processing unit that accesses the model and displays the model on the display of the workstation. The software further includes navigation tools, e.g., typed commands, icons and/or graphical devices superimposed on the displayed model, that enables a user to manipulate the model on the display and simulate the movement of at least one tooth in the model relative to other teeth in the model in three-dimensional space, and quantify the amount of movement precisely. This simulation can be used, for example, to design a particular target situation for the patient.

The development of a unique target situation for the patient has utility in a variety of different orthodontic appliances, including an approach based on off-the-shelf or generic brackets and a custom orthodontic archwire. The scope of the invention is sufficient to encompass other types of appliances, such as an approach based on customized brackets, retainers, or the removable aligning devices mentioned earlier. In a bracket embodiment, the memory contains a library of virtual, three-dimensional orthodontic brackets. The software permits a user to access the virtual brackets through a suitable screen display, and place the virtual brackets on the virtual model of the dentition of the patient. This bracket bonding position can be customized on a tooth by tooth basis to suit individual patient anatomy. Because the tooth models, brackets and archwire are individual objects, and stored as such in memory, the treatment planning apparatus can simultaneously display the virtual brackets, the archwire and the virtual model of the dentition, or some lesser combination, such as just the brackets, just the dentition, or the brackets and the archwire but not the teeth. The same holds true with other appliance systems.

In a preferred embodiment, the virtual model of teeth comprises a set of virtual, individual three-dimensional tooth objects. A method of obtaining the tooth objects from a scan of teeth, and obtaining other virtual objects of associated anatomical structures, e.g., gums, roots and bone is described. When the teeth are separated from each other and from the gums, they can be individually manipulated. Thus, the individual tooth objects can be individually selected and moved relative to other teeth in the set of virtual tooth objects. This feature permits individual, customized tooth positioning on a tooth by tooth basis. These positioning can be in terms or angular rotation about three axis, or translation in transverse, sagittal or coronal planes. Additionally, various measurement features are provided for quantifying the amount of movement.

One of the primary tools in the treatment planning apparatus is the selection and customization or a desired or target archform. Again, because the teeth are individual tooth objects, they can be moved independently of each other to define an ideal arch. This development of the target archform could be calculated using interpolation or cubic spline algorithms. Alternatively, it can be customized by the user specifying a type of archform (e.g, Roth), and the tooth are moved onto that archform or some modification of that archform. The archform can be shaped to meet the anatomical constraints of the patient. After the initial archform is designed, the user can again position the teeth on the archform as they deem appropriate on a tooth by tooth basis. The treatment planning software thus enables the movement of the virtual tooth objects onto an archform which may represent, at least in part, a proposed treatment objective for the patient.

Numerous other features are possible with the treatment planning software, including movement of the teeth with respect to the other teeth in the archform, changing the position of the virtual brackets and the teeth with respect to each other, or opposing teeth with respect to the selected archform. Custom archwire bends can be simulated to provide additional corrections. Bonding corrections at the bracket-tooth interface are also possible.

In another aspect of the invention, a method is provided for digital treatment planning for an orthodontic patient on a workstation having a processing unit, a user interface including a display and software executable by the processing unit. The method comprises the steps of obtaining and storing a three-dimensional virtual model of teeth representing the dentition of the patient in a current or observed situation. The virtual model is displayed on the display. The method further includes the step of moving the position of teeth in the virtual model relative to each other so as to place the teeth of the virtual model into a target situation and displaying the virtual model with the teeth moved to the target situation to the user. Parameters for an orthodontic appliance to move the patient's teeth from the current situation to the target situation can be derived from the virtual model and the target situation. For example, if virtual brackets are placed on the teeth, their location in the target situation can dictate the design of an archwire to move the teeth to the target situation.

In a preferred embodiment, the method includes the step of providing screen displays on the display enabling a user of the workstation to operate the user interface so as to place virtual three-dimensional objects representing orthodontic appliances, e.g., brackets, onto the surface of teeth in the virtual model. A library of the virtual brackets can be stored in memory and a landmarking procedure used to place the brackets on the teeth at the desired location. Anatomical considerations may dictate movement of the brackets from their originally selected position to a new position.

Accordingly, the software provides navigational tools enabling a user to change the position of the brackets relative to the teeth.

The treatment planning system is based on individual tooth objects which can be moved to any position in three dimensional space. They can be moved in several ways—by direct user specified movement, and by adding an object comprising an orthodontic appliance and changing the configuration of the appliance to cause the teeth to move. For example brackets can be virtually bonded to the teeth and the position of the brackets changed in three dimensions to move the teeth. Alternatively, an archwire shape can be defined which fits into the slots i the brackets. Movement of the archwire can be simulated, resulting in a simulation of tooth movement.

The treatment planning software includes features enabling more accurate diagnosis. For one thing, the virtual model of the dentition can be manipulated in three dimensions at will, resulting in complete visual assessment of the model. Measurement tools are also provided by which the orthodontist can determine the distance between any two points on the model. This allows the user to quantify the patient's morphology both at initial and at target stages. Thus, treatment progress, proposed changes in appliance design, or tooth movement can be quantified precisely. By measuring the differences and changes in morphology during the care cycle, the orthodontist can quickly and accurately assess patient treatment. Changes in treatment can be made early on. The result is shorter treatment times (and the ability for the orthodontist to service more patients per year).

The treatment planning system incorporates virtual objects comprising orthodontic appliances that may be used to treat the patient. The invention provides for design of complete appliance systems and simulation of various appliance designs and associated tooth movement, in a computer-interactive fashion.

These and many other features of the presently preferred embodiment of the treatment planning apparatus and method are set forth below.

BRIEF DESCRIPTION OF THE DRAWINGS

FIG. 19 also shows the various parameters by which the orthodontist can adjust the shape of the arch, the distance between the teeth, the distance between the molars, and other parameters, so as to provide a unique and customized archform for the patient.

DETAILED DESCRIPTION OF PREFERRED EMBODIMENT

Figure 1:
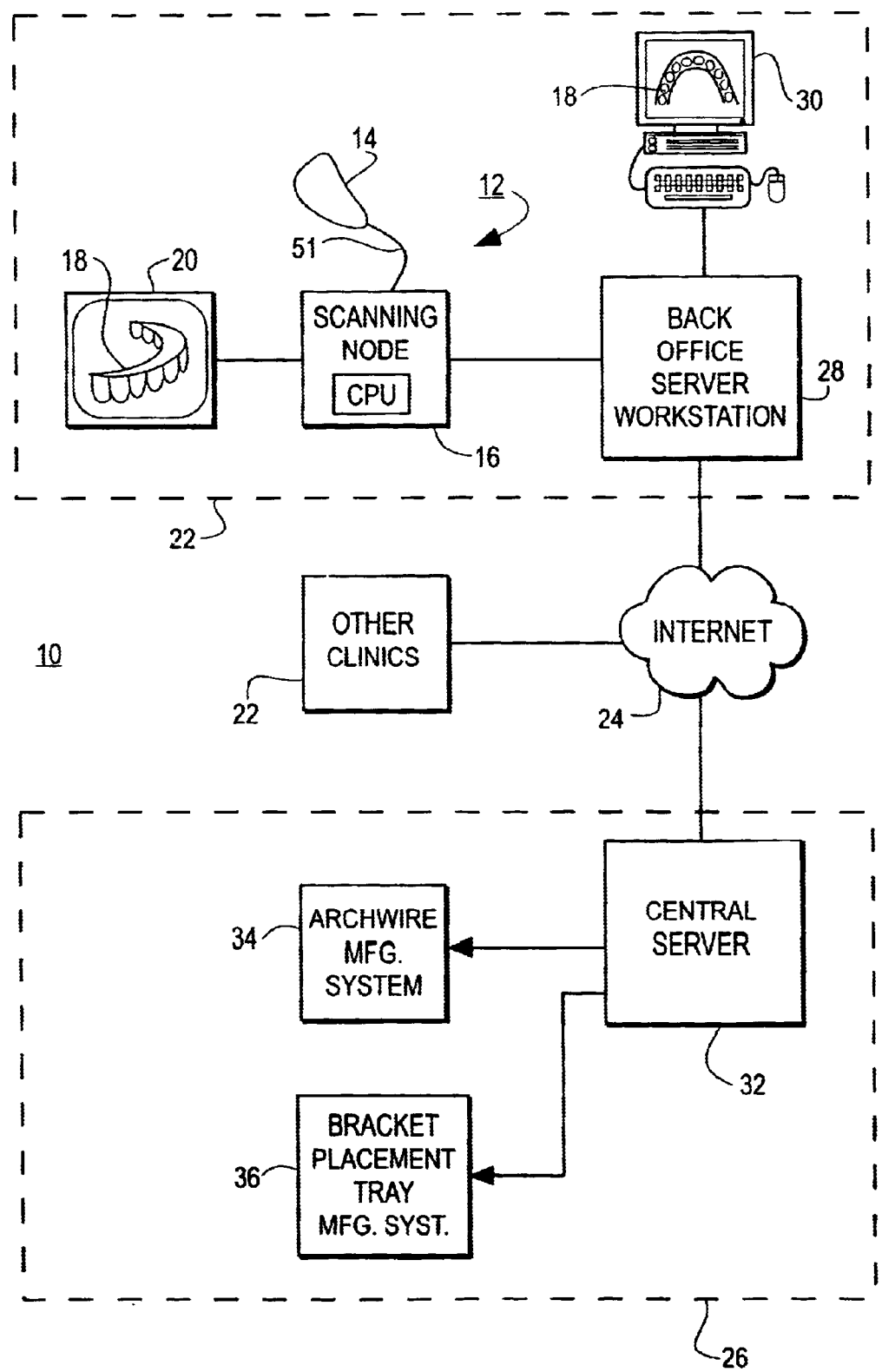
FIG. 1 is an illustration of an orthodontic care system incorporating a hand-held scanner system and treatment planning software in accordance with a representative embodiment of the invention. The hand-held scanner is used by the orthodontist to acquire three-dimensional information of the dentition and associated anatomical structures of a patient and provide a base of information for interactive, computer software-based diagnosis, appliance design, and treatment planning for the patient. The scanner is suitable for in-vivo scanning, scanning a plaster model, scanning an impression, or some any combination thereof.

The present invention provides a dental treatment planning method and apparatus that allows for the design of virtually any configuration of tooth objects, bracket objects, wire objects and other appliances and objects. In essence, the treatment planning features is in the nature of a computer-aided design and computer-aided manufacturing (CAD/CAM) system that allows the user to identify treatment goals and to specify appliances that will achieve these goals.

Whereas in the prior art Andreiko et al. patents the treatment goals and appliance design were mathematically derived from measurements of the malocclusion, with little or no user involvement, the present invention provides an interactive treatment planning system in which the tools are provided to the orthodontist to play an active role in diagnosis, treatment planning and appliance design. For example, the orthodontist can change the configuration for the archform, can correct individual tooth positions on the archform on a tooth by tooth basis, change the bracket position on the teeth, and can add additional bends in the archwire.

The orthodontic treatment planning can work with any three-dimensional tooth objects, regardless of their source. In the illustrated embodiment, the three dimensional objects comprise tooth objects obtained from a scanning of the dentition of the patient. The manner of developing these three-dimensional tooth objects is described at length in the patent application of Rudger Rubbert et al. filed Apr. 13, 2001, entitled SCANNING SYSTEM AND CALIBRATION METHOD FOR CAPTURING PRECISE THREE-DIMENSIONAL INFORMATION OF OBJECTS Ser. No. 09/834,593, the contents of which are incorporated by reference herein. Other possibilities are 3-D models obtained from CAT scans, laser scans, ultrasound, 3-D photogrammetry of models, or other type of scanning taken either in-vivo or from a plaster model, or some combination of these techniques.

In the illustrated embodiment, the treatment planning system also uses three-dimensional objects comprising virtual models of orthodontic appliances, such as brackets and orthodontic archwires. The bracket models can be obtained as CAD models from bracket manufacturers, or from a scanning of the brackets themselves. The wire models can be derived from the cross-sectional shape and length of the wire, and parameters as to the shape of an arch that the wire is representing (including loops), as described below. Obviously, in other types of orthodontic treatment scenarios where brackets are not used, other types of virtual three-dimensional objects may be used, such as retainers, Herbst appliances, the substantially transparent, removable aligning devices commercialized by Align Technologies, etc.

The treatment planning that will be performed by the user for a given patient will necessarily vary from patient to patient. The preferred embodiment of the treatment planning method provides a wealth of viewing, measuring, and simulation tools by which the orthodontist can plan treatment for any given patient. For ease of understanding and clarity, the treatment planning software will be mainly described in terms of screen displays that are displayed on a user interface and the key functionality in the screen displays. A person skilled in the art will be able to program a computer to provide these functions from the present description and representative screen displays.

It is contemplated that most if not all aspects of the treatment planning software will ordinarily be installed on a back office server or workstation in an orthodontic clinic. The software may also be located in other clinics of related specialties, such as periodontal clinics, family dental clinics, and clinics of oral surgeons, so that the treatment planning, patient virtual model, and other parameters can be shared amongst multiple users. Some functionality of the software may not be available or used where the software is distributed among multiple specialties. For example, the periodontist may not have any desire to change or modify tooth position or archwire shape. To facilitate interaction regarding the patient at clinics of various specialties, it is desirable to equip each clinic or office with the scanning system described herein (or other suitable scanner), for treatment monitoring purposes, and so that when a new patient arrives at any of the clinics they can be scanned and the digital model shared with other specialties.

It is possible that some or all of the treatment planning software could be installed at a remote site and some or all of the treatment planning done remotely, e.g, by a central service center, by a remotely located orthodontist, or by a precision appliance service center as described below. In this latter scenario, the three-dimensional model of the malocclusion and necessary patient information is transmitted over a suitable communications link (e.g. the Internet) to the remote location. An orthodontist or other trained person operating the software at the remote location separates the teeth from the surrounding anatomical structures to create a set of independent tooth objects, studies the malocclusion and the treatment objectives for the patient, and uses the software to arrive at an initial proposed target situation for the patient. The initial proposed target situation is sent back to the orthodontist for review, modification, and/or approval. The model can be reviewed simultaneously and interactively with the patient, or shared with other specialists, or with a precision appliance manufacturing center.

To carry this out, a copy of the digital model of the target situation (or of the malocclusion) is maintained on a central server at one location, such as the remotely located precision appliance manufacturing center. The users access that copy of the model over the Internet and manipulate it using the treatment planning software described herein. All users that simultaneously participate in interactive, simultaneous manipulation of the model view the same thing. The copy of the model that is stored in the orthodontist's office remains unchanged.

Before explaining these software tools and the treatment planning in detail, an overview of a presently preferred orthodontic care system in which the invention may be practiced will be described initially.

Overview

FIG. 1 is an illustration of an orthodontic care system 10 incorporating a scanner system 12. The scanner system 12 includes a hand-held scanner 14 that is used by the orthodontist to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional virtual computer model 18 of the dentition. The computer model provides the orthodontist and the treatment planning software with a base of information to plan treatment for the patient. The model 18 is displayed to the user on a monitor 20 connected to the scanning node 16.

The illustrated orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program, described at length below. The software obtains the three-dimensional digital data of the patient's teeth from the scanning node and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket position. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22.

The system is applicable to other types of orthodontic appliances. For example, a target situation for the dentition could be transferred to the precision appliance service center 26. The center 26 could make a stereolithographic (SLA) model of the dentition. From that model (or from models of the malocclusion), the center could fabricate removable orthodontic appliances such as transparent aligning devices, retainers, Herbst expansion devices, etc. using known techniques.

As shown in FIG. 1, the precision appliance service center 26 includes a central server 32, an archwire manufacturing system 34 and a bracket placement manufacturing system 36. These details are not particularly important to the treatment panning methods and apparatus and are therefore omitted from the present discussion for sake of brevity. For more details on these aspects of the illustrated orthodontic care system, the interested reader is directed to the patent application of Rudger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, the contents of which are incorporated by reference herein.

Scanner System and Acquiring Three-Dimensional Model

Figure 2:
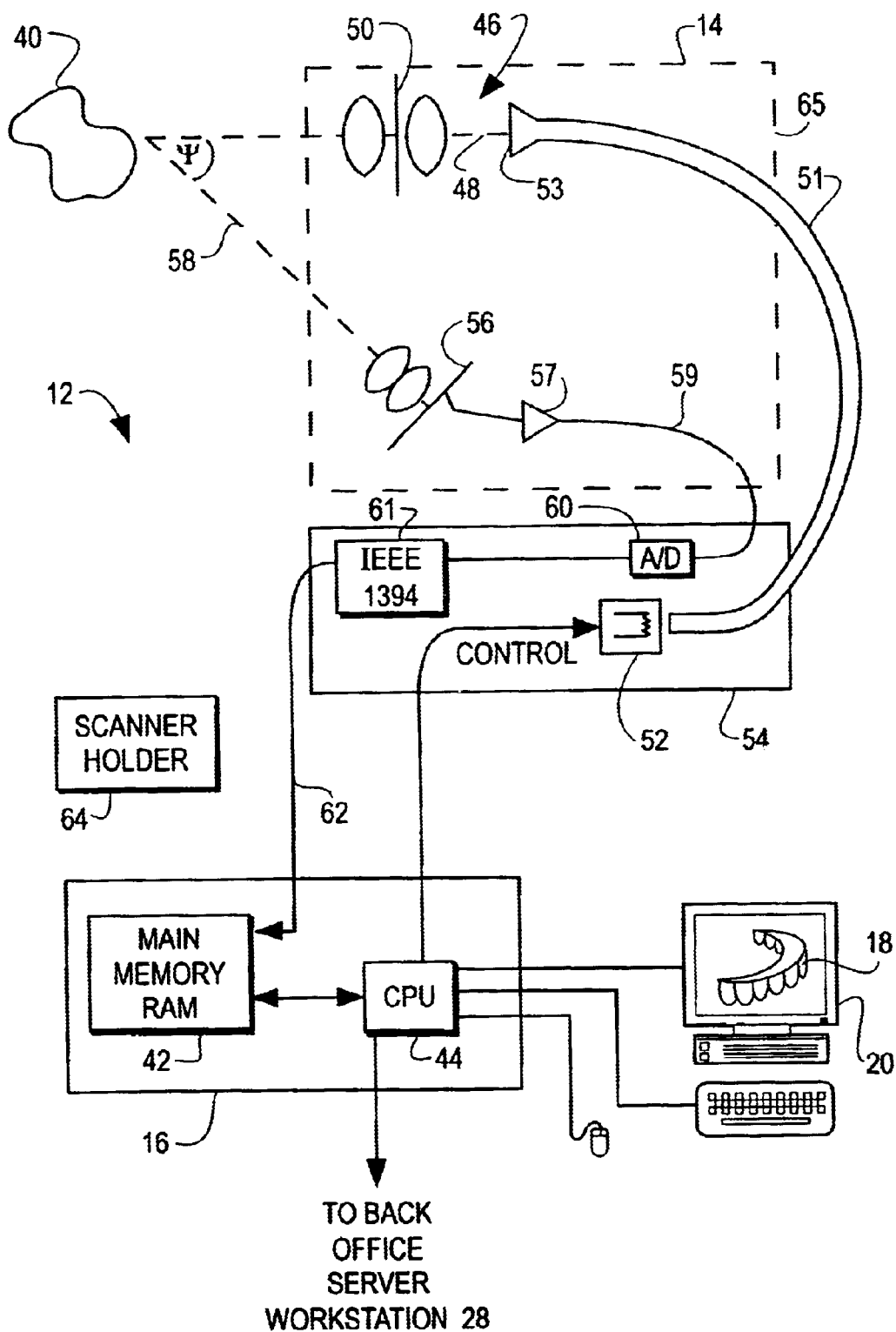
FIG. 2 is a block-diagram of a scanning system, suitable for use in the orthodontic care system of FIG. 1.

FIG. 2 is a more detailed block-diagram of the scanning system 12, suitable for use in the orthodontic care system of FIG. 1. The scanning system 12 is a mechanism for capturing three-dimensional information of an object 40, which in the present example is the dentition and surrounding anatomical structures of a human patient, e.g., gums, bone and/or soft tissue. The scanning system 12 includes a scanner 14 which is used for image capture, and a processing system, which in the illustrated example consists of the main memory 42 and central processing unit 44 of the scanning node or workstation 16.

The scanner 14 includes a projection system 46 that projects a pattern onto the object 40 along a first projection axis 48. The projected pattern is formed on a slide 50 which is placed in front of a light source 53. In the illustrated embodiment, the light source 53 comprises the terminus of a fiber-optic cable 51. The cable 51 carries a high intensity flash generated by a flash lamp 52 located in a base unit 54 for the scanner. A suitable flash lamp is the model FX-1160 flash unit available from Perkin Elmer. The illuminations of the flash lamp 52 cause the pattern contained in the slide 50 to be projected onto the three-dimensional surface of the object. Further details on the types of patterns suitable for the pattern are set forth in the following co-pending patent applications of Rüdger Rubbert et al:, Ser. No. 09/254,755 filed Mar. 9, 1999; Ser. No. 09/560,131 filed Apr. 28, 2000, Ser. No. 09/673,863 filed Nov. 30, 2000 assigned to the assignee of the present invention, the contents of which are incorporated by reference herein. A presently preferred projection pattern is described below. The details on the optics of the projection system 46 are set forth in further detail below.

The scanner 14 further includes an electronic imaging device 56 comprising an array of photo-sensitive pixels. A preferred embodiment is an off-the-shelf, color-sensitive, charged-coupled device (CCD) of a size of 1,028×1,028 pixels arranged in an array of rows and columns. The Sony ICX205AK CCD chip is a suitable electronic imaging device. The electronic imaging device 56 is oriented perpendicular to a second imaging axis 58, which is off-set from the projection axis 48. The angle $\Psi$ between the projection and imaging axes need not be known in a preferred embodiment of the invention. However, if the 3D calculations are made in accordance with the parameters of FIG. 9, then the angle and the separation distance between the center of the imaging device 56 and the center of the light source 53 need to be known.

The angle $\Psi$ will be optimized during design and manufacture of the scanner depending on the desired resolution required by the scanner. This, in turn, is dependent on the degree to which the surface under scrutiny has undercuts and shadowing features which would result in the failure of the imaging device to detect the projection pattern. The greater the angle $\Psi$, the greater the accuracy of the scanner. However, as angle $\Psi$ increases, the presence of undercuts and shadowing features will block the reflected pattern and prevent capture of the pattern and subsequent three-dimensional analysis of those portions of the surface. Angle $\Psi$ is shown somewhat exaggerated in FIG. 2, and will generally range between 10 and 30 degrees for most applications.

The electronic imaging device 56 forms an image of the projection pattern after reflection of the pattern off of the surface of the object 40. The reflected patterns imaged by the imaging device contain three-dimensional information as to the surface of the object, and this information needs to be extracted from the images. The scanning system therefore includes a processing subsystem which is used to extract this information and construct a three-dimensional virtual model of the object 40. In the preferred embodiment, this processing subsystem consists of a memory 42 storing calibration information for the scanner, and at least one processing unit, such as the central processing unit 44 of the scanning workstation 16. The location of the memory and the processing unit is not important. They can be incorporated into the scanner 14 per se. Alternatively, all processing of the images can take place in the back office server 28 or in another computer. Alternatively, two or more processing units could share the processing in order to reduce the amount of time required to generate the three-dimensional information.

The memory 42 stores a calibration relationship such as a table for the scanner 14. The calibration table comprises information used to compute three-dimensional coordinates of points on the object that reflected the projection pattern onto the imaging device. The information for the table is obtained during a calibration step, performed at the time of manufacture of the scanner 14. The calibration table includes an array of data storage locations that contain two pieces of information. Firstly, the calibration table stores pixel coordinates in X and Y directions for numerous portions of the projection pattern that are imaged by the electronic imaging device 56, when the pattern is projected onto a calibration surface at two different distances during a calibration procedure. Secondly, the table stores distance information, (e.g., in units of tenths of millimeters), in X and Y directions, for the portions of the projection pattern imaged at the two different distances.

The scanning system requires at least one processing unit to perform image processing, three-dimensional calculations for each image, and registration of frames to each other. The processing unit 44 in the illustrated embodiment is the central processing unit (CPU) of the scanning work station 16. The CPU 44 processes the image of the pattern after reflection of the pattern off the surface of the object 40 and compares data from the image to the entries in the calibration table. From that comparison (or, more precisely, interpolation relative to the entries in the table, as explained below), the processing unit 44 derives spatial information, in three dimensions, of points on the object that reflect the projected pattern onto the electronic imaging device.

Basically, during operation of the scanner to scan an object of unknown surface configuration, hundreds or thousands of images are generated of the projection pattern as reflected off of the object in rapid succession. For each image, pixel locations for specific portions, i.e., points, of the reflected pattern are compared to entries in the calibration table. X, Y and Z coordinates (i.e., three dimensional coordinates) are obtained for each of these specific portions of the reflected pattern. For each picture, the sum total of all of these X, Y and Z coordinates for specific points in the reflected pattern comprise a three-dimensional "frame" or virtual model of the object. When hundreds or thousands of images of the object are obtained from different perspectives, as the scanner is moved relative to the object, the system generates hundreds or thousands of these frames. These frames are then registered to each other to thereby generate a complete and highly accurate three-dimensional model of the object 40.

Stray data points are preferably canceled out in generating the calibration table or using the calibration table to calculate three-dimensional coordinates. For example, a smoothing function such as a spline can be calculated when generating the entries for the calibration table, and the spline used to cancel or ignore data points that deviate significantly from the spline.

FIG. 2 also shows a few other features of the presently preferred scanning system 12. After the CCD imaging device 56 captures a single image, the analog voltage signals from the device 56 are amplified in an amplifier 57 and fed along a conductor 59 to an analog to digital converter 60. The digital signal is converted into a bitmap stream of digital image data. The data is formatted by a module 61 into an IEEE 1394 "firewire" format for transmission over a second conductor 62 to the main memory 42 of the scanner work station 16. The scanning system includes an optical scanner holder 64 for the user to place the scanner after the scanning of the dentition is complete. These details are not particularly important and can vary considerably from the illustrated embodiment. As noted earlier, preferably the scanning system is constructed to provide a minimum of equipment and clutter at the chair side. Hence, the scanning station is preferably located some distance away from the chair where the patient sits. The cable leading from the scanner 14 to the base station and/or workstation 16 could be suspended from the ceiling to further eliminate chairside clutter.

The scanning work station 16 also includes the monitor 20 for displaying the scanning results as a three-dimensional model of the dentition in real time as the scanning is occurring. The user interface also includes a keyboard and mouse for manipulating the virtual model of the object, and for entering or changing parameters for the scanning, identifying sections or segments of scans that have been obtained, and other features. The scanning station may also include a foot switch, not shown, for sending a signal to the CPU 44 indicating that scanning is commencing and scanning has been completed. The base station may alternatively include a voice recognition module that is trained to recognize a small set of voice commands such as START, STOP, AGAIN, REPEAT, SEGMENT, ONE, TWO, THREE, FOUR, etc., thereby eliminating the need for the foot switch. Scanner start and stop commands from the CPU 44, in the form of control signals, are sent to the light source 52, thereby controlling the illumination of the lamp 52 during scanning.

The light source 52 operates at a suitable frequency, such as 6 flashes per second, and the frame rate of the CCD imaging device 56 is synchronized with the frame rate. With a frame rate of 6 flashes per second, and a scanning motion of say 1–2 centimeters per second, a large of overlap between images is obtained. The size of the mirror at the tip 68 of the scanner influences the speed at which scanning is possible. The illustrated embodiment of the mirror at the tip 68 is 18 mm square. A larger mirror reflects more surface of the object and enables faster scanning. A smaller mirror requires slower scanning. The larger the mirror, the more difficult in-vivo scanning becomes, so some trade-off between size and utility for in-vivo scanning exists. The mirror 18 is heated to prevent fogging during in vivo scanning by a resistance heater coil.

This overlap between images generated by the scanner 14, and resulting three dimensional frames, allows a smooth and accurate registration of frames relative to each other. The frame rate and permissible rate of scanner motion will depend on many factors and can of course vary within the scope of the invention. A preferred frame rate will be at least one flash per second. Flashing a high intensity flash lamp for a brief period of time is a preferred embodiment since it is desirable to reduce the exposure time of the CCD imaging device 56 to reduce blurring. A high intensity lamp is desirable to achieve sufficient signal strength from the imaging device. A preferred embodiment uses 5 $\mu$sec flash times with similar exposure periods. An alternative embodiment would use a constant illumination source of high intensity, and control exposure of the imaging device using a shutter, either a physical shutter or using electronic shutter techniques, such as draining charge accumulating in the pixels prior to generating an image. Scanning using longer exposures would be possible without image blur, using electronic image motion compensation techniques described in Lareau, et al., U.S. Pat. No. 5,155,597.

Figure 3:
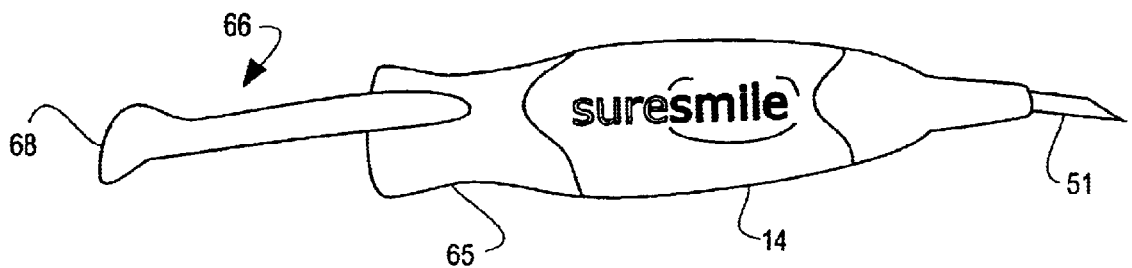
FIG. 3 is a perspective view of a hand-held scanner used to acquire information of an object under scrutiny, suitable for use in the orthodontic care system of FIG. 1.

FIG. 3 is a perspective view of a hand-held scanner 14 used to acquire information of an object under scrutiny, suitable for use in the orthodontic care system of FIG. 1. The projection system 46 and the electronic imaging device 56 of FIG. 2 are contained in the housing 65 for the scanner. The housing 65 is sized and shaped to be held in a human hand. The scanner 14 includes an elongate distal portion 66 and a tip 68. The tip 68 is sized and shaped such that it can be inserted into and moved within an oral cavity of a human so as to enable scanning of anatomical structures inside the oral cavity. A heated mirror (not shown) is placed on the underside of the tip 68 to direct the projection pattern from the optics of the scanner onto the object and to direct the reflected pattern from the object towards the imaging optics associated with the electronic imaging device.

Figure 4:
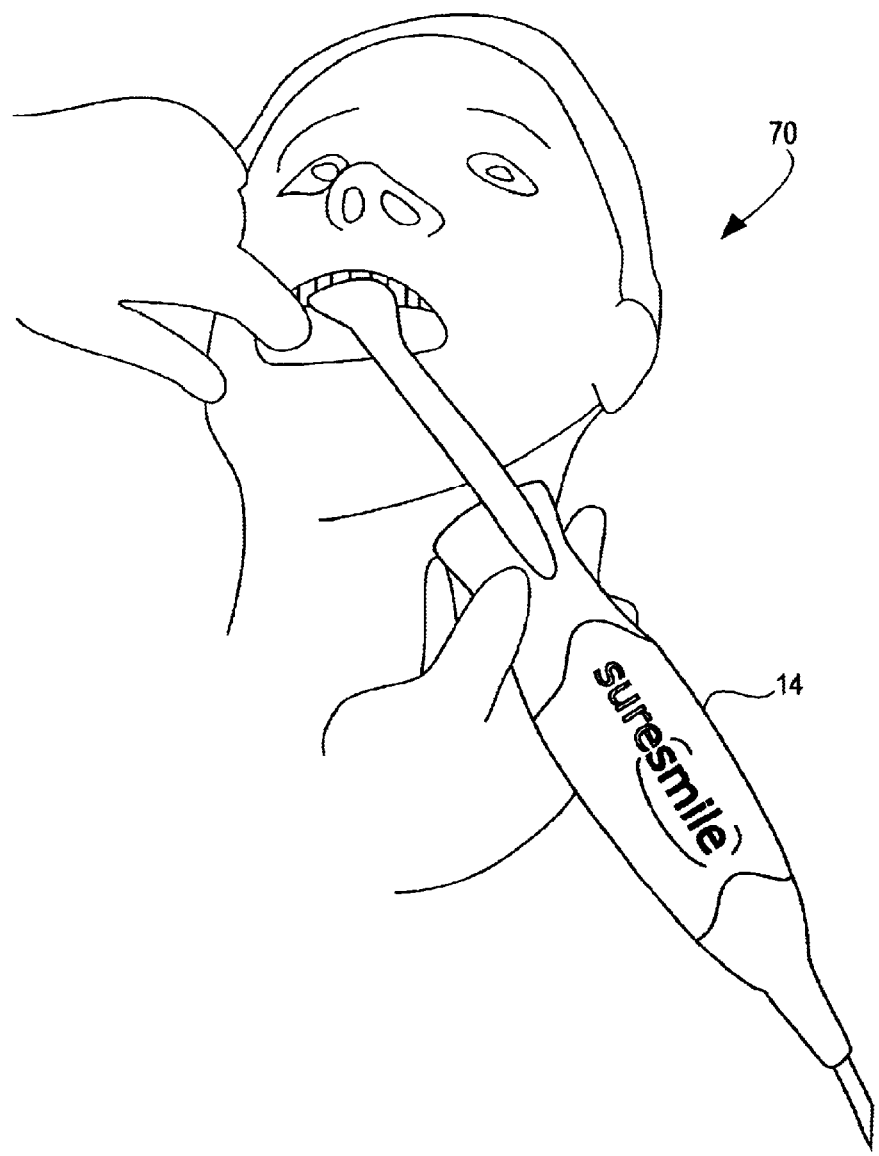
FIG. 4 is an illustration of a patient being scanned with the hand-held scanner of FIG. 3.

FIG. 4 is an illustration of a patient 70 being scanned with the hand-held scanner 14 of FIG. 3. The checks and lips are retracted from the teeth and the tip 68 of the scanner is moved over all the surfaces of the teeth in a sweeping motion at a velocity of perhaps 1–2 centimeters per second. The entire upper or lower jaw may need to be scanned in a series of scans, one for the left side, one for the right side, and one for the front. These individual scans are registered to each other to complete a registration of an entire upper or lower arch. Activation of the foot switch (not shown), or recognition of voice commands, indicates to the scanning processing system when each scanning segment is initiated and terminated. The entire process takes just a few minutes. Depending on the color and translucency of the object and the illumination intensity and frequency of the light source in the scanner, it may be necessary to apply a very thin coating of a bright reflective substance such as titanium dioxide to the teeth. If the scan is of a plaster model, the scanning can be done in one continuous scan eliminating the need for scanning in segments and registering segments together.

Figure 5:
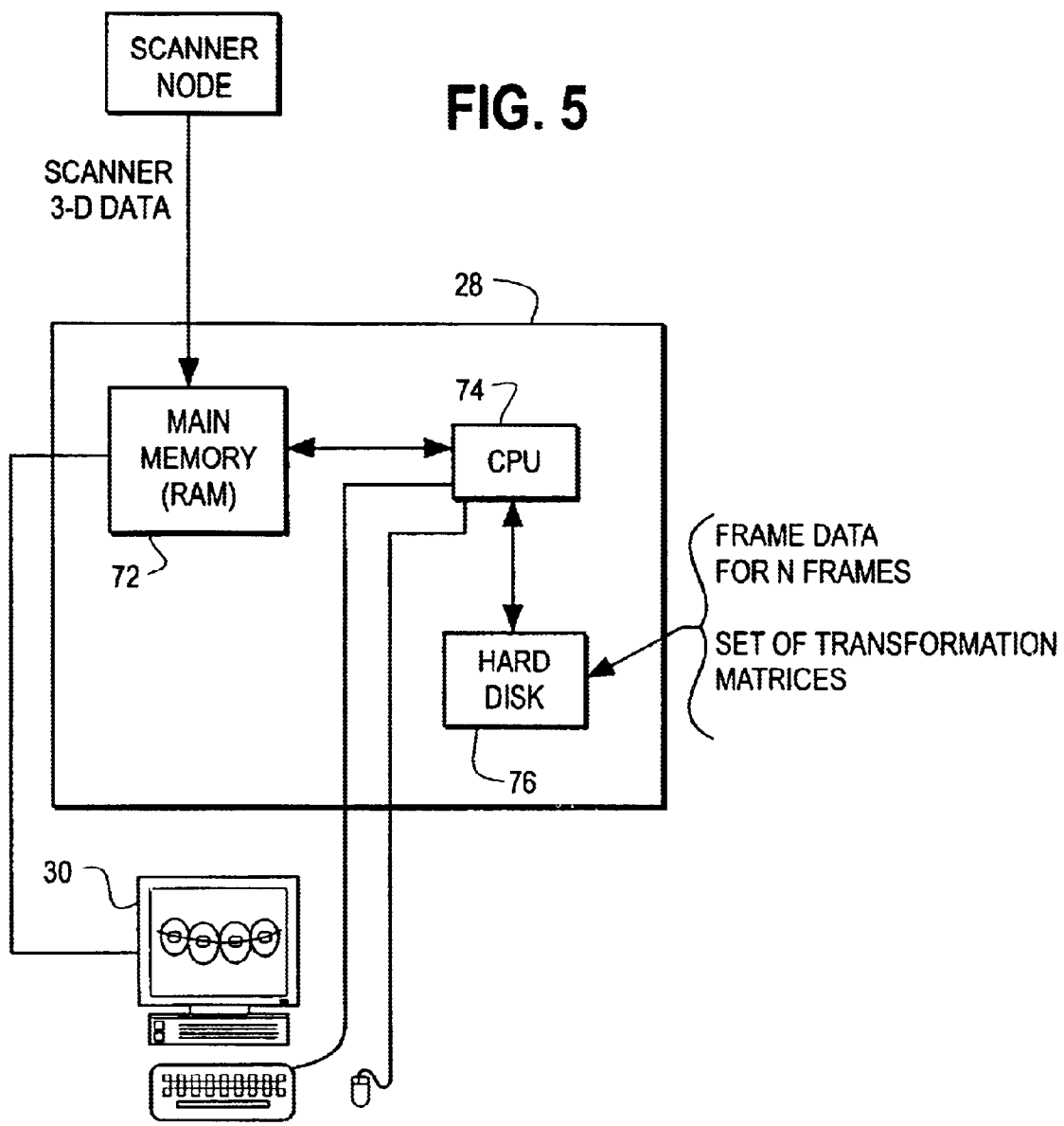
FIG. 5 is a block diagram of the back office server of FIG. 1 showing the elements used to calculate the digital model of the patient's dentition and display the digital model on a screen display of the back office server.

FIG. 5 is a block diagram of the back office server of FIG. 1 showing the elements used to calculate the digital model of the patient's dentition. After the scanning workstation has processed all the images captured by the scanner and generated a set of three dimensional frames, the frame data is transmitted to the back office server. The back office server 28 performs a cumulative registration process for the frames and ultimate generates and displays the digital model on a screen display 30. The raw scanner data in the form of three-dimensional frames is stored in the main computer memory 72. The frame data for N captured images from the scanner is stored in the hard disk 74. The hard disk also stores a set of N transformation matrices $[T]_i$, for $i=2-N$. The transformation matrices basically contain information as to how each frame of three-dimensional points needs to be translated and rotated in a three-axis Cartesian coordinate system in order to be registered with the other frames in a best-fit manner.

Further details on the construction, operation and calibration of the scanner, the calculation of 3-D point clouds from each captured image, and registration of frames to generate a complete three dimensional model of the dentition is described in further detail in the patent application of Rudger Rubbert et al., entitled SCANNING SYSTEM AND CALIBRATION METHOD FOR CAPTURING PRECISE THREE-DIMENSIONAL INFORMATION OF OBJECTS filed Apr. 13, 2001, Ser. No. 09/834,593, the contents of which are incorporated by reference herein. At noted above, the treatment planning features are applicable to a three-dimensional model of the dentition derived from any source, including CAT scans, laser scans taken from dental impressions, models or otherwise, and ultrasound. The hand-held optical scanner described herein offers numerous advantages, particularly it allows scans to be obtained in real time very quickly, i.e., in a matter of minutes. The scans can be taken fully from the mouth or from a model, or from some combination of the two.

After the three-dimensional model of the upper and lower arch is obtained, the teeth in the model are virtually extracted from the surrounding anatomical structures and represented as individual three-dimensional tooth objects. One way of performing this is described below.

Landmarking

Figure 6:
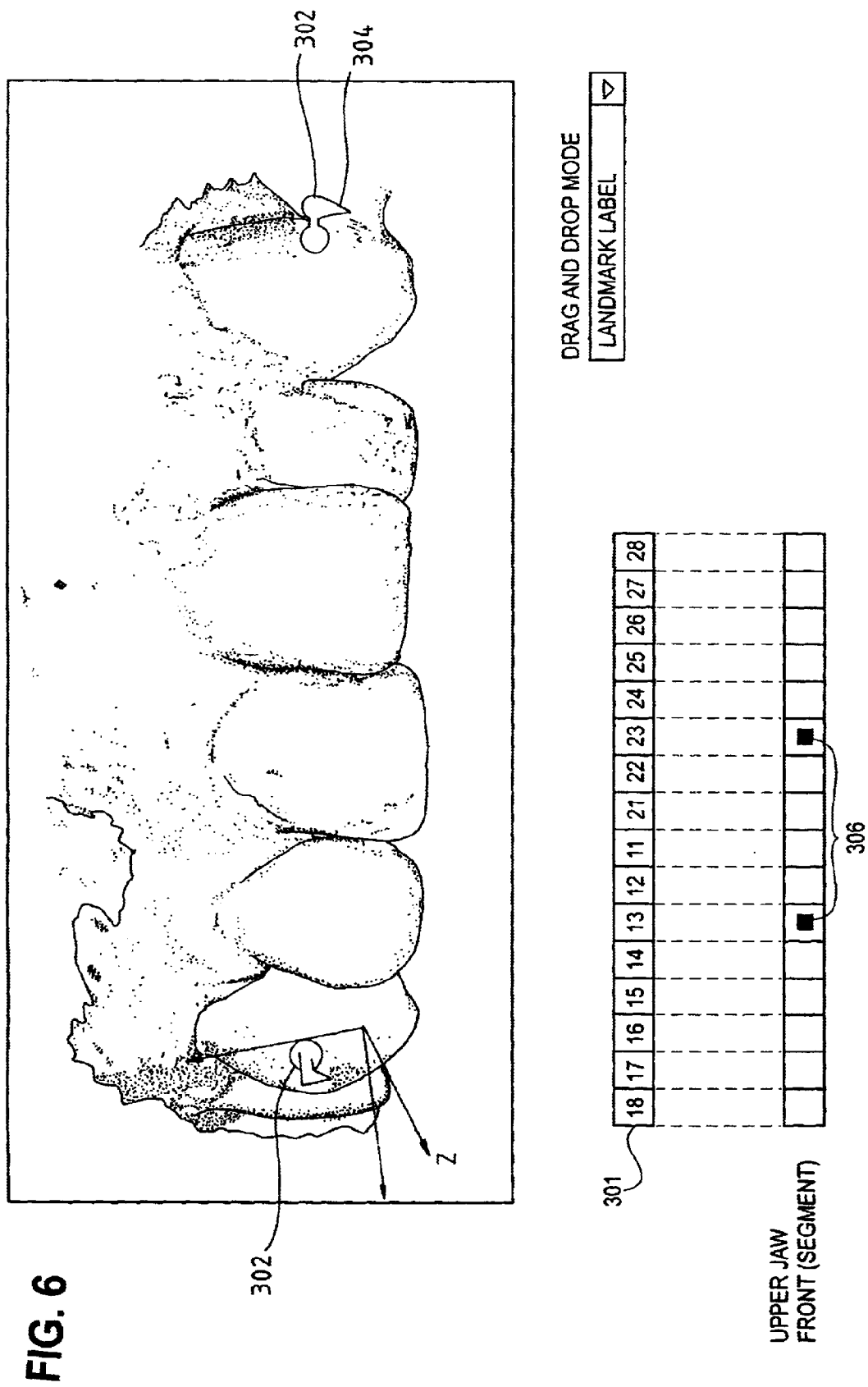
FIG. 6 is a screen shot displayed on the display of the back office server of FIG. 1, showing a graphical representation of a three-dimensional model of a patient's upper front teeth after a frame to frame registration. The user is applying landmarks to the teeth as a preliminary step in treatment planning, and as a step in registering overlapping segments of a scanned upper jaw relative to each other to calculate a complete model of the upper jaw and associated dentition.

FIG. 6 is a screen shot showing a graphical representation of a three-dimensional model of a patient's upper front teeth representing one scan (segment 1) after a frame to frame registration. The user is applying landmarks 302 to the canine teeth as a preliminary step in treatment planning, and as a step in registering overlapping segments of a scanned upper jaw relative to each other to calculate a complete model of the upper jaw and associated dentition.

The purpose of the landmarking shown in FIG. 6 is to select a point on the canine teeth which is common to the front scan and the two side scans. The landmarking is also done at a point on the labial surface of the teeth that would be a suitable location for placement of an orthodontic bracket as part of an appliance to correct a malocclusion. To place the landmarks, the user clicks on a tooth number, indicated by the row of numbers 301, and drags the cursor with a mouse to the surface on the canine teeth where they wish to place the landmark. They then release the cursor, and the landmark 302 appears on the tooth. The landmark has an arrow 304, which must point to the incisal edge of the tooth. The user can rotate the landmark to place the arrow in the proper orientation by simply clicking on the landmark and turning the mouse one way or the other. As each landmark is placed, a box below the tooth number is highlighted as indicated at 306.

Alternatively, the software can place the landmarks automatically after the user has placed initially just two or three landmarks, preferably two landmarks at the molars and one of the front teeth. Having those landmarks, the system knows the general direction of the tooth axes, since tooth axes are generally parallel in most instances. The system also knows some idea of tooth widths as for most humans there is a fairly close relationship between the widths of the teeth. For example, someone with wide molars will as a rule have wide front teeth as well and thus the distance from the molar landmark to the front landmark will indicate the tooth width for the patient. So, the system will be able to make good guesses regarding tooth positions from this information. As the landmarks can slide along the surface of the dentition, we could after initial placement automatically slide the landmark along the surface of a tooth and detect the midpoint or center of the curvature of the labial tooth surface, which will come fairly close to where the landmark needs to be placed.

The tooth numbering convention shown in FIG. 6 is as follows: the first number indicates the quadrant of the patient's dentition, with 1 being upper right, 2 being upper left, 3 being lower left, 4 being lower right. The second number is the tooth number in the quadrant with 1 being the incisor. Thus, the landmarks 302 are placed at teeth 13 and 23, the upper canines.

Since these canines overlap their respective side scan, and since the X, Y and Z coordinates of the point on the labial surface of the tooth where the landmark is placed is assigned in the computer, it is now possible to register the front segment shown in FIG. 57 to the two side segments. This segment registration is now performed. The overlapping frames between each segment can be registered to each other, or to the entire other segment.

After segment registration is performed, a cumulative registration of the entire jaw is performed in accordance with the procedures set forth in the application of Rüdger Rubbert et al., SCANNING SYSTEM AND CALIBRATION METHOD FOR CAPTURING PRECISE THREE-DIMENSIONAL INFORMATION OF OBJECTS filed Apr. 13, 2001, Ser. No. 09/834,593. After the cumulative registration is performed, a virtual, three-dimensional model of the entire jaw is presented to the orthodontist on the monitor in the back office server workstation 28 (FIG. 1).

In planning treatment for the patient, the orthodontist conceptualizes teeth as individual teeth objects which can be moved independently of each other to correct the patient's malocclusion. Furthermore, orthodontists are trained to make physical models of the patient's dentition from an impression, cut the teeth from the model, and then individually move the teeth relative to each other to provide a target situation which corrects for the malocclusion. Therefore the back office server workstation preferably includes a software which enables the orthodontist to do this with the virtual three-dimensional model of the patient's dentition. In order to do this preliminary step in treatment planning, it is highly desirable therefore to process the three dimensional model (resulting from a cumulative registration of frames) by separating the virtual teeth from the surfaces representing the gums and other anatomical structure, and presenting the crowns of the teeth to the orthodontist. Alternatively, roots of teeth from a template of three-dimensional template roots can be associated with each tooth. The roots could also come wholly or partially from 2-D sources such as X-rays of the roots, or from a 3-D source such as ultrasound or CAT scanner. The tooth separation process allows individual teeth to be moved independently in three dimensions on the computer in an interactive, user-specified manner, since they are individual three-dimensional objects. This process of separation of the teeth from the cumulative registration into individual teeth objects will be described next.

The separation process described below has one further advantage, namely requiring less memory to represent an individual tooth. Cumulative registration may result in an extremely large number of points from a large number of frames to represent any given tooth. The separation process, as described below, reduces this data set to a single set of points that describe a single surface representing the surface of the tooth. Much less memory is required. Consequently, the treatment planning software can process treatment planning steps for the teeth more quickly.

Separation of Teeth into Individual Tooth Objects

FIGS. 7A–7F are a series of illustrations showing the generation of an individual tooth model from a scanned tooth. The process will now be explained in detail.

Figure 7A:
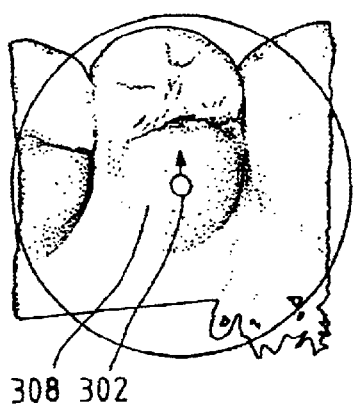
FIGS. 7A–7F are a series of illustrations showing the generation of an individual tooth model from a scanned tooth, shown in FIG. 7A, and a template tooth, shown in FIG. 7B. A library of template teeth similar to FIG. 7B are stored as three-dimensional computer models in computer memory. The individual tooth model is a three-dimensional tooth object having a single set of points defining the boundaries of the tooth. The individual tooth model reduces the amount of data required to represent the tooth, as compared to the data representing the tooth after a cumulative registration of a large number of frames.
Figure 7B:
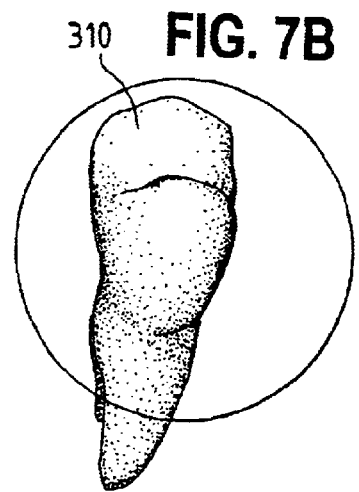
Figure 7C:
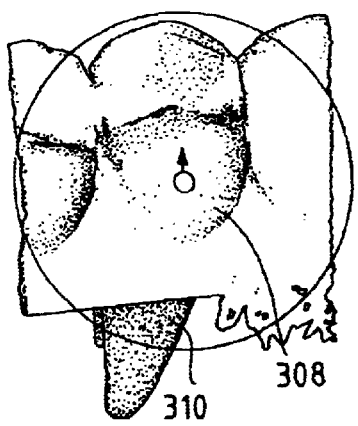

FIG. 7A shows the scanned dentition and associated anatomical structure surrounding the tooth 308. This tooth is tooth number 14 in the numbering convention shown in FIG. 6. The back office server workstation stores a three-dimensional template tooth for each tooth in the maxilla and the mandible. The template tooth 310 for tooth number 14 is shown in FIG. 7B. The template tooth 310 is a three-dimensional tooth object having a single set of points defining the boundaries of the tooth. As shown in FIG. 7C, the template tooth 310 is positioned approximately in the same location in space as the tooth 308. The landmark 302 assists in providing the proper axial rotation of the template tooth to have it fit properly with respect to the tooth 308. The template tooth is placed at the point cloud of the dentition according to the labial landmark. The template tooth can be scaled larger or smaller or positioned arbitrarily by the user using object navigation tools, described below, in order to get a close a position as possible to the point cloud of the dentition.

Figure 7D:
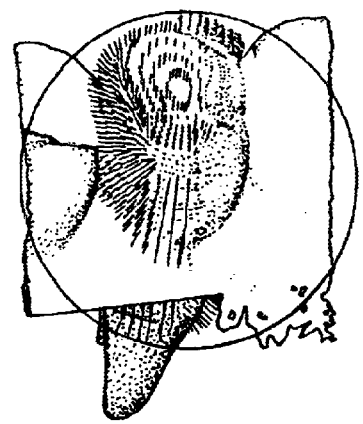
Figure 7E:
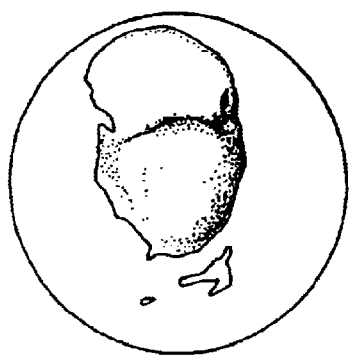
Figure 7F:
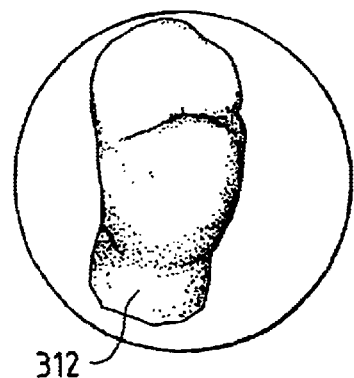

As shown in FIG. 7D, vectors are drawn from the points on the template tooth to the scanned point cloud of the tooth 308. Every ray intersects several surfaces, the number of surfaces depending on how often the respective part of the surface has been covered during scanning. For each vector, a surface is selected. Preferably, the smallest triangle surface is selected, since this surface corresponds to an image taken by the scanner when the scanner was positioned in a more perpendicular orientation to the surface, resulting in more accuracy in the determination of the coordinates of that portion of the surface. As another possibility, the outermost surface is selected, using a filter to insure that no extraneous surfaces are used. These points of the surfaces intersected by all the vectors are combined as newly generated triangle surfaces and therefore form one consistent surface shown in FIG. 7E. Then, finally, missing parts of the tooth are completed from the template tooth. The result is shown in FIG. 7F as virtual tooth object 312. In a second pass, this generated object 312 is then used as a template tooth, and the steps indicated by FIG. 7C, 7D and 7E are repeated in an iterative fashion. This is done to make sure that the algorithm works even if there are differences between the original template tooth and the scanned point cloud.

Figure 8:
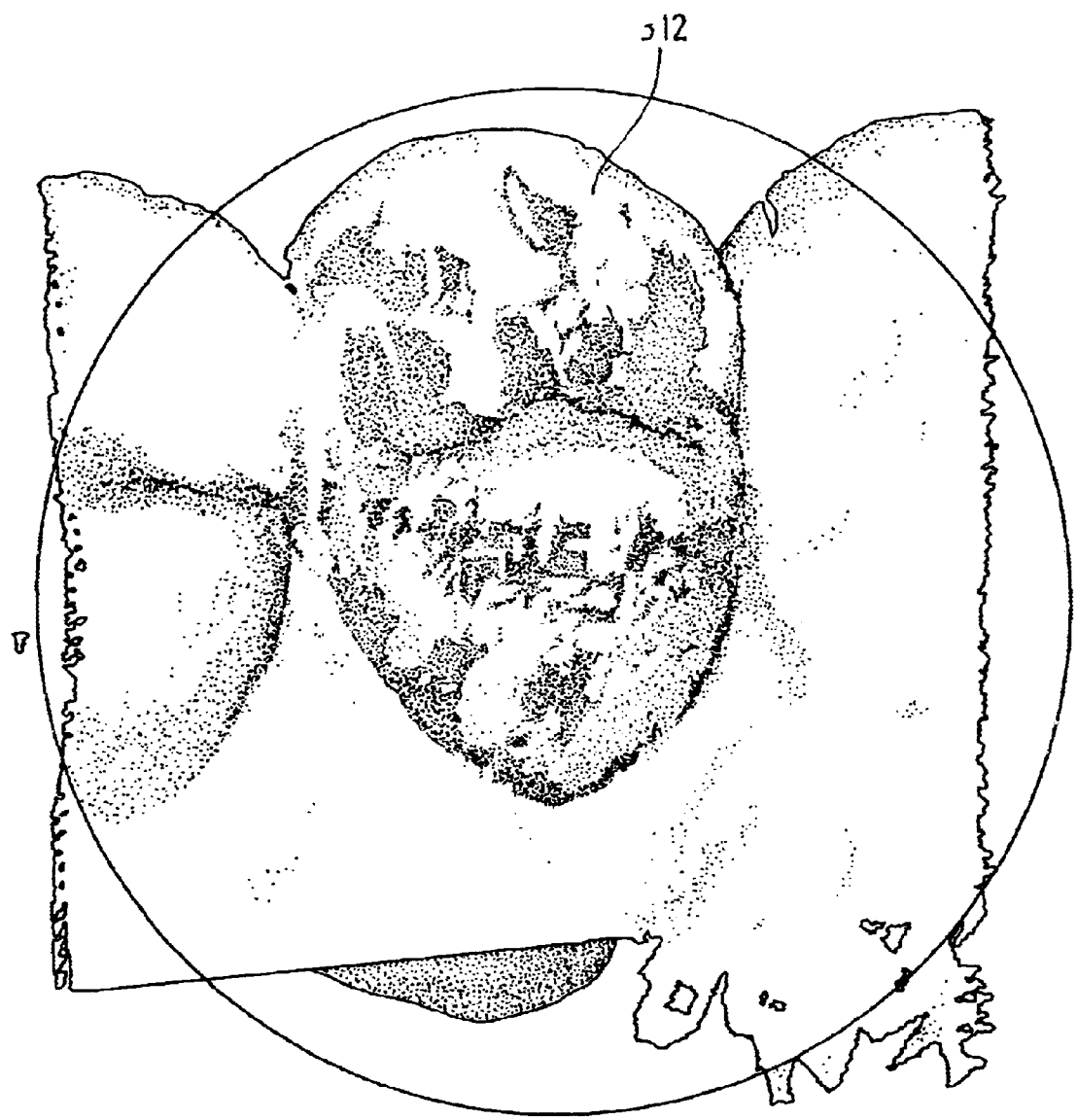
FIG. 8 is an illustration of the tooth model of FIG. 7D positioned in the computer model of the patient's dentition, surrounded by other anatomical structures.

The final result, an individual tooth object 312, is then displayed to the user, as shown in FIG. 8. The tooth object 312 is displayed as a three-dimensional superposition of the original data (white) and the separated model of the tooth (darker tones). These tones allow the user to ascertain whether there is an even distribution of white and dark tones, indicating a good fit between the scanned tooth and the tooth template. The final result can also just be simply displayed for the user.

This process is of course performed for all the teeth. The result is a set of individual tooth objects for all the teeth in the patient's dentition. The teeth can be displayed either alone, or in conjunction with the surrounding anatomical structures such as shown in FIG. 8.

The virtual model of the patient's dentition, and the individual tooth objects created as explained above, provides a base for diagnostic analysis of the dentition and treatment planning. A bite registration scan is obtained from the patient at the onset of treatment to spatially correlate the scans of the upper and lower jaws when the dentition is clenched. This scan is used to provide a registration of the upper and lower jaw to determine the correct upper and lower relative position. This bite registration scan may be performed during treatment to monitor progress.

Because the tooth separation process indicated by FIG. 7A–7F can be somewhat time consuming if there is a substantial amount of human interaction involved, it may be desirable to automate the process or off-load this function to other computer and human resources. For example, the library of template teeth could be stored at a computer at the precision appliance service center. The clinics forward the scan data of the malocclusion (either before or after a registration) to the appliance service center. A trained technician at the appliance service center operates the software described in conjunction with FIGS. 7A–7F on an appliance service center computer. The technician provides any required user input required by the software (such as checking the position of the template tooth relative the scan data and modifying the position of the template tooth). After the process is complete, a set of individual tooth objects is obtained. This set of tooth objects (data representing three-dimensional point clouds for all the teeth in the dentition) is sent back to the clinic 22 and stored on the back-office server 28. The precision appliance service center could also perform other treatment planning functions, such as, for example, generating an initial target situation for the teeth and forwarding it to the orthodontist for revision, initial bracket placement, etc.

Initial Virtual Bracket Placement

With the individual teeth now cut from the three-dimensional model of the dentition and represented as tooth objects, they can be moved relative to each other in three dimensions. Since orthodontics assumes that a bracket is fixedly bonded to a tooth, by moving the bracket one moves the tooth. The next step in the process is thus selecting an initial location to bond the brackets to the tooth. As noted below, this initial location can be adjusted by the treatment planning software. The spatial location of the surfaces of the bracket and the surfaces of the corresponding tooth are known. Collision avoidance algorithms are used to keep the bracket positioned on the surface of the tooth and prevent the virtual bracket from entering the tooth itself, a clinically undesirable result. The user is able to move the bracket independently of the tooth by activating an icon (such as one shaped like a magnet to signify the mating of the bracket to the tooth). When the bracket is moved to the new location, the tooth matches up to the surface of the bracket.

The brackets are represented in the software as virtual three-dimensional objects, and the surface of all the brackets and the teeth are known in three dimensional spatial coordinates. Accordingly, collision detection algorithms are employed to detect when simulated tooth or bracket movement would result in a collision between brackets and teeth. Similar collision algorithms are provided to prevent the adhesion surface of the bracket from migrating into the body of the virtual tooth object and to keep the brackets located on the surface of the teeth. IF the user wishes to move the location of the brackets, the movement of the teeth follows the movement of the bracket. Also, again since the bracket is a three-dimensional virtual object with known spatial coordinates, the user is provided with a tool (such as an icon) which when activated allows the user to move the bracket about one plane or axis, and freeze the movement in the other directions.

Initial virtual bracket placement is done as follows. Landmarks 302 such as shown in FIG. 6 are placed on the labial surfaces of all the teeth. The landmarks are placed at the location where the orthodontist expects to place an orthodontic bracket to correct the malocclusion. The bracket shape is shown on the monitor. Three-dimensional templates for a variety of commercially available brackets are stored in memory and the software asks the orthodontist to select a particular manufacturer and style of bracket to use with the patient. Thus, as the landmarks 302 are placed, virtual brackets appear in the computer model on the labial surfaces of the teeth where the orthodontist desires to place the brackets. The orthodontist can move the bracket position depending on the type of forces the orthodontist wishes to create on teeth to correct the malocclusion. Because the brackets are individual objects and stored in memory, when they are placed on the surface of virtual teeth complete position information is known in three dimensions. As such, the brackets can be displayed either alone, or in conjunction with teeth, or hidden from view, by means of appropriate user specified commands on the user interface. For example, the screen display showing the target or current stage can have an icon indicating hide brackets, or display brackets, and activating the icon causes the brackets to be hid or displayed. The same is true for other virtual objects that exist independently of other objects, such as tooth models and the archwire.

With the teeth now separated into individual tooth objects, and the orthodontist can now view the current target stage, custom design a target situation for the patient, and design the appliance to treat the malocclusion. These aspects will now be described in further detail.

Viewing the Observed (Current) Stage

Figure 12:
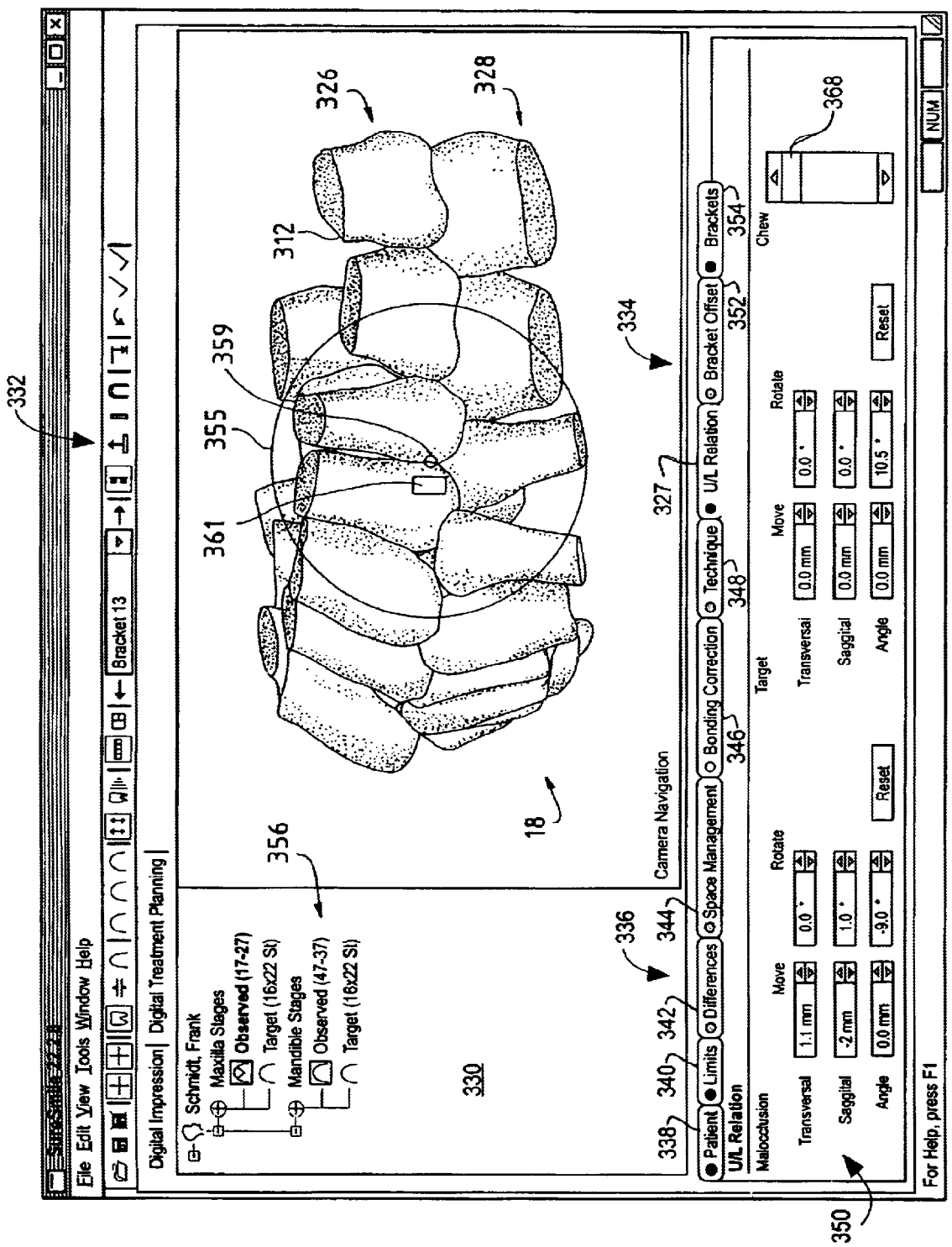
FIG. 12 is a screen shot from the treatment planning software showing a set of individual tooth objects representing the observed stage of a patient suffering from a malocclusion.

FIG. 12 is a screen shot showing a three-dimensional model 18 of a malocclusion, showing the teeth 312 in both the upper and lower arches 326 and 328, respectively. The screen 330 includes a row of icons 332 across the upper portion of the display, which are associated with various tools available to the user to view the dentition, virtual brackets, and current and target archforms. The lower portion 334 of the screen includes a set of tabs 336 that are accessed in various aspects of treatment planning. These tabs 336 include a patient tab 338, which accesses the screen of FIG. 9. A limits tab 340 allows a user to breakdown the tooth movement between observed and target stages into stages, such as 30 percent, 50 percent and 75 percent, and display the tooth positions for both arches at these positions. A differences tab 342 quantifies the differences (in terms of translation and rotation) between the observed and target stages for each tooth. The space management tab 344 permits the user to simulate extraction of one or more teeth and adjust the spacing between teeth in either arch. A bonding correction tab 346 allows for adjustment of tooth position to be realized via bonding corrections. The technique tab 348 allows the user to select a bracket prescription and default settings for bracket height (distance from bracket slot to incisal edge of tooth). The tab also displays the parameters for the bracket prescription chosen by the user. The upper/lower (U/L) relations tab 327, selected in the screen shot of FIG. 12, allows the user to modify the relation of the upper and lower jaws, by both translation in three axes (transversal, sagittal and vertical directions) and by rotation about these axes. The user manually enters values in the field 350 to change any parameter, and the change is immediately reflected in the view of the model of the dentition.

The tabs also include a bracket offset tab 352 that allows a user to reposition the bracket on a tooth and specifies numerical values for each bracket placement modification. A brackets tab 354 allows a user to enter information as to the type or manufacturer of brackets for each tooth in the both arches.

A further "morphing" tab could be provided which would animate the movement of the teeth from malocclusion to target situations based on treatment steps or limits defined by the user (explained in further detail below).

The screen shot of FIG. 12 also includes a region 356 that allows the user to navigate between views of the observed stage and views of the target stage. Here, the user has highlighted or selected both arches in the observed stage, so the screen display shows the model of the dentition in the current or observed stage.

Figure 10:
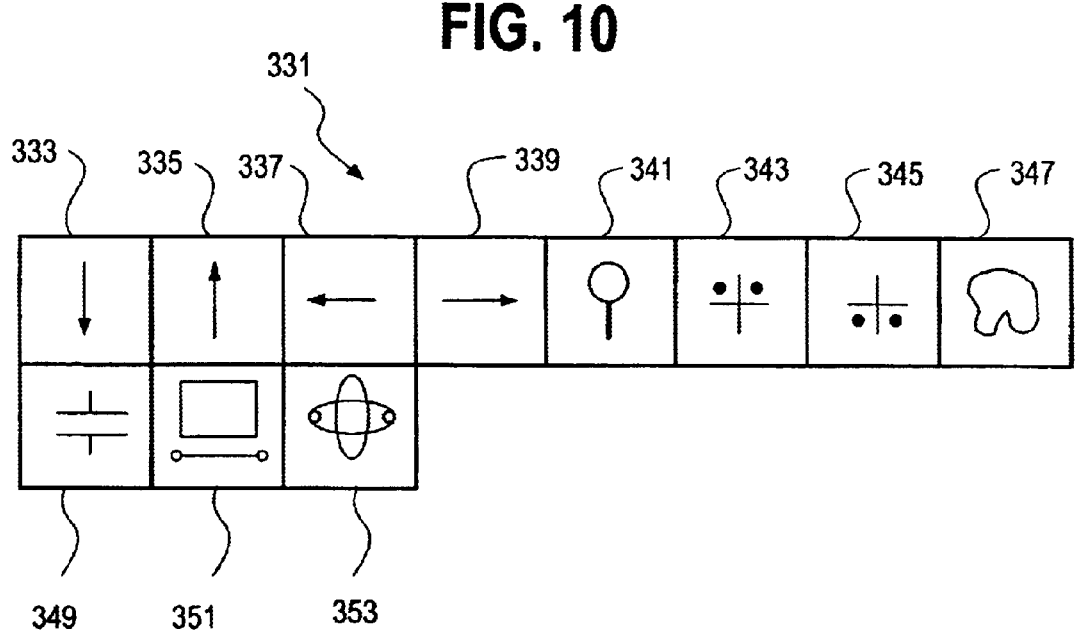
FIG. 10 is an illustration of a series of icons that appear on a screen display that provide some tools for viewing the three-dimensional model of the patient's dentition.

Referring to FIG. 10, the treatment planning software preferably displays a plurality of icons 331, not all of which are shown in FIG. 12, to enable the user to quickly and easily view the three dimensional model in various standard perspectives. For example, the icons 331 of FIG. 10 include icons 333, 335, 337 and 339 for viewing the dentition in top, bottom, right hand side and left hand side views, respectively. An icon 341 is provided which zooms in or out. Icons 343 and 345 allow the user to select for viewing just the upper or lower arches, respectively, including virtual teeth, virtual brackets and virtual archwire. The icon 347 allows the user to show or hide the virtual dentition, excluding brackets and archwires. An icon 349 allows the user to select or deselect the virtual brackets. A marker icon 341 is used for measurement functions (described below) and an object navigation icon 353 is used for manipulating any of the virtual objects on the screen.

Figure 13:
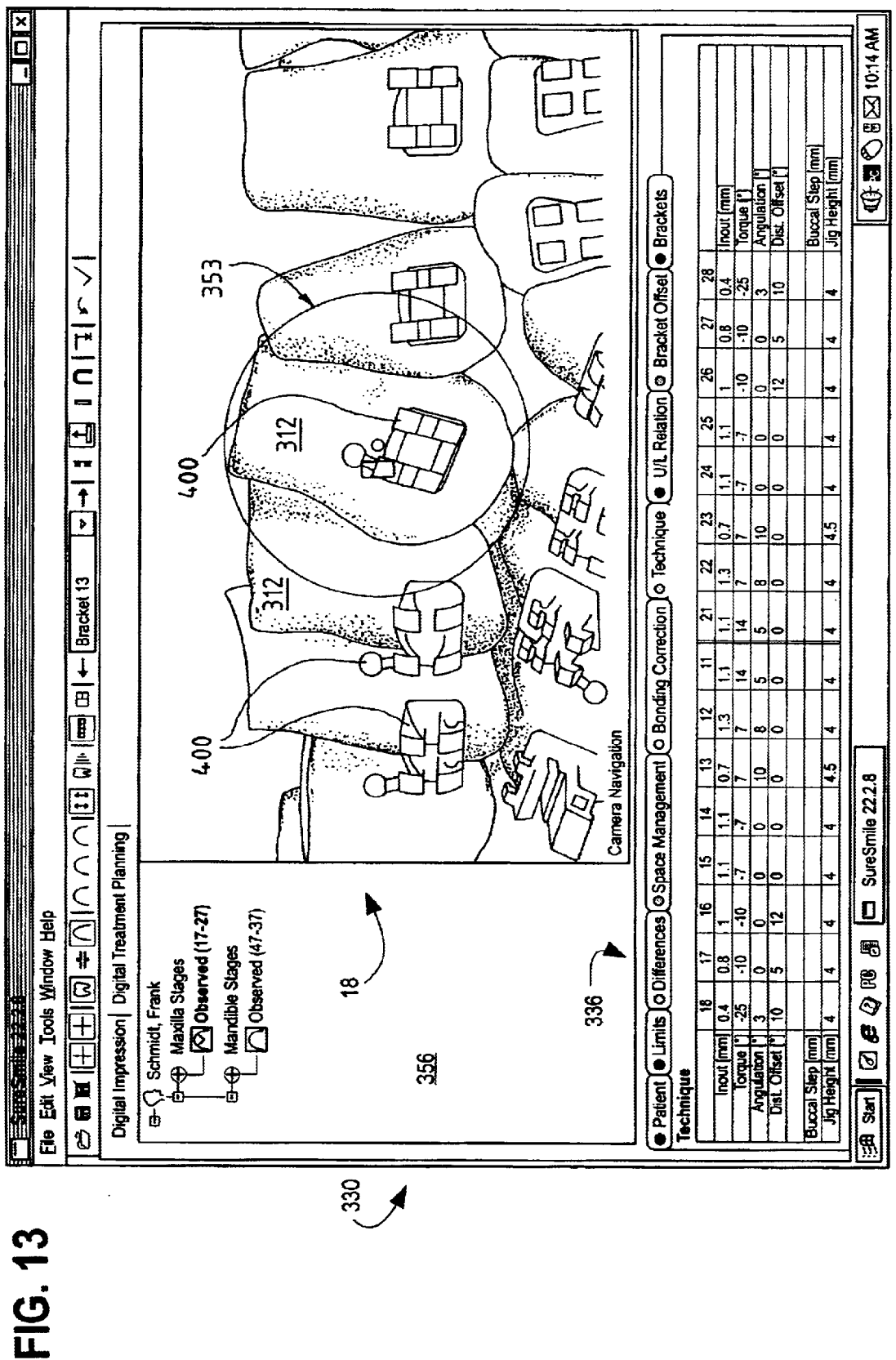
FIG. 13 is another screen shot from the treatment planning software, showing the observed stage and the placement of virtual three-dimensional brackets on the surfaces of the teeth.

When positioning multiple objects in the three-dimensional view, such as shown in FIG. 12, the camera navigation icons of FIG. 10 move all the elements together. As shown in FIG. 13, the initial placement of the virtual brackets 400 can be displayed along with the teeth. Further, the camera navigational tools allow the user to zoom in an zoom out in any desired degree. However, the virtual teeth 312 and virtual brackets 400 are individual three-dimensional objects which can be selected and moved independently. One way of moving objects is by entering new positional values (e.g, in terms of mm of displacement or angle of rotation, as described later). Another method provided by the software is using object navigational controls, activated by clicking the icon 353 or by accessing the function via a tools menu. The object navigation controls allow the user to move the object based on orthodontic judgment and visual feedback. The amount of movement is stored and can be displayed using numerical position information. As will be discussed in further detail below, the bracket position can be individually adjusted on a tooth by tooth basis. Furthermore. the camera navigation icons permit navigation of the archforms (i.e., the teeth placed on some selected archform), navigation of the brackets, or navigation of the archwire.

The object navigation tools first require an object (e.g., tooth, bracket, archwire, etc.) to be selected. To select and deselect any object displayed on the screen, the user places the cursor over the object and double clicks the mouse. The selected object is highlighted in a separate color. Additional objects are selected by pressing and holding down the <CTRL> button while double clicking additional objects. To magnify the object, the object is selected as described above and the icon 341 is clicked.

Figure 11:
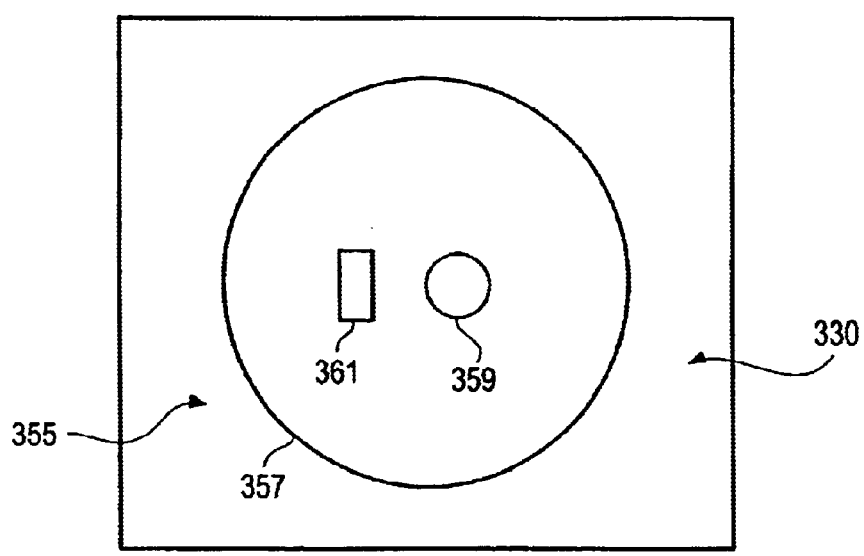
FIG. 11 is an illustration of a set of icons which are part of the screen displays which act as a navigational tool and allow the user to manipulate the three-dimensional models of teeth and brackets on the display.

To move the selected objects, the software provides an object navigation icon 353. When the icon 353 is selected, object navigational tools appear on the screen 330. These navigational tools 355 are shown in FIG. 11 and FIG. 12. The object navigational tools 355 comprise a large circle 357, a small circle 359 and a small rectangle 361. First, the object is selected as described above. Then, the object navigation icon 353 is clicked, activating the tools 355 such that they are displayed. The user then positions the mouse pointer relative to the tools 355 and presses and drags as described below to position the object. When the mouse pointer is outside the large circle 357, when they start dragging the object is turned either clockwise or counterclockwise depending on the direction of dragging. When the mouse pointer is positioned within the large circle 357, when they start dragging they rotate the object in any direction. When they start dragging from inside the small circle 359, the object is moved in one plane. When they start dragging from inside the rectangle 361, by dragging down the object is moved closer, by dragging upward the object is moved farther away.

Measuring Objects

Referring again to FIG. 10, the icon 351 allows the user to establish a measurement marker on any portion of the virtual model of the dentition. The user uses the icon 351 to place markers at any two points on the dentition and the distance between the markers is displayed on the screen.

To use the icon 351, the user clicks on the icon, and then clicks anywhere in the 3-D view of the dentition to place markers. A straight line is drawn between two markers. The distance between the markers appears on the screen, e.g., at the upper left hand corner of the windowpane of the 3-D view. A tool in the Tools menu in includes a DELETE ALL MARKERS function to delete the markers.

The measurement function allows the user to measure tooth size, inter-molar width, inter-canine width, the arch length, curve of spee, and other important orthodontic and diagnostic parameters. The measurement aspect of the invention is particularly significant in that it permits precise quantification of simulated tooth movement, both in terms of establishing initial treatment plan as well as monitoring treatment.

Viewing Cross-Sections of Model

Figure 16:
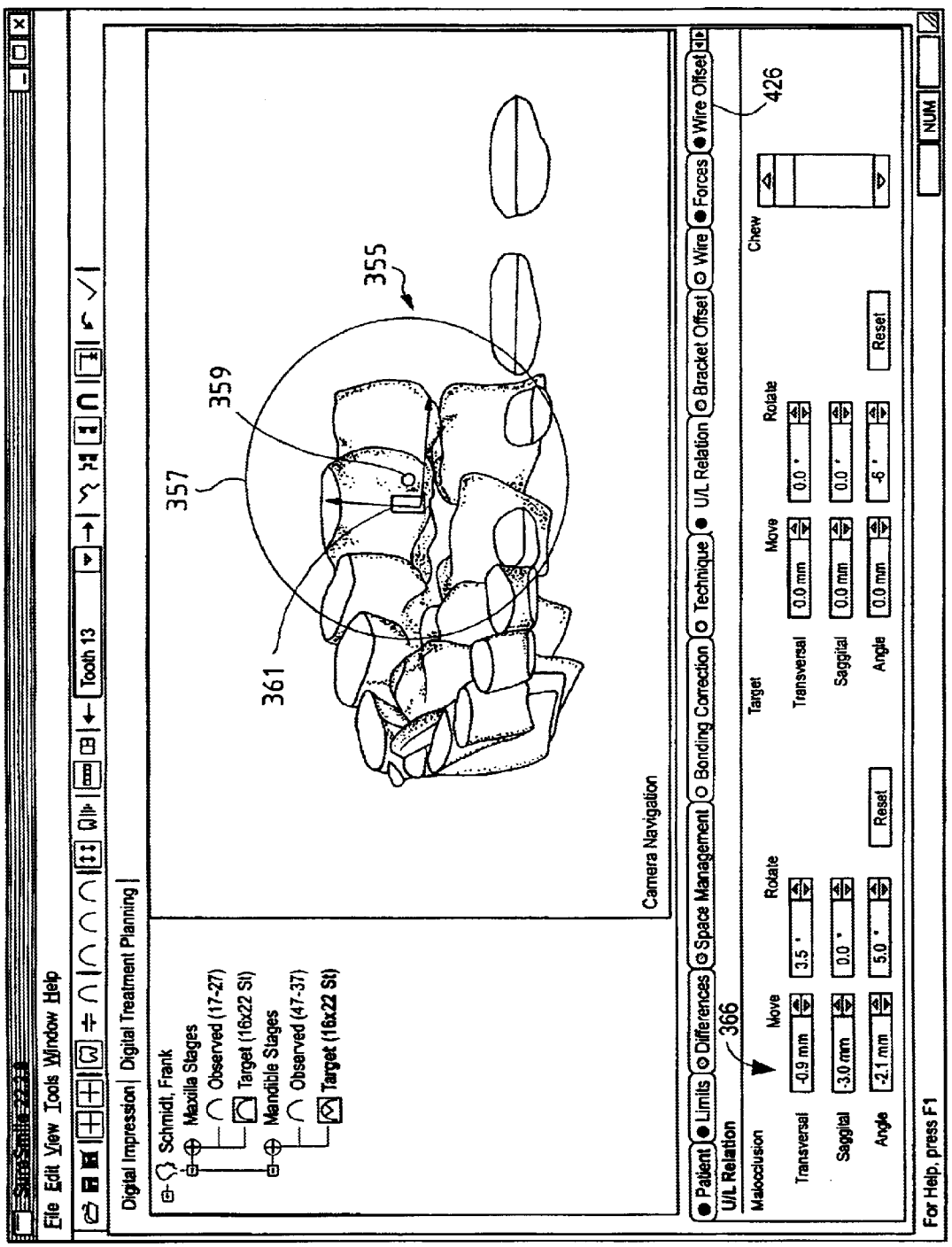
FIG. 16 is a screen show showing a cross-section or "clipping plane" view through the upper arch in a target situation.
Figure 17:
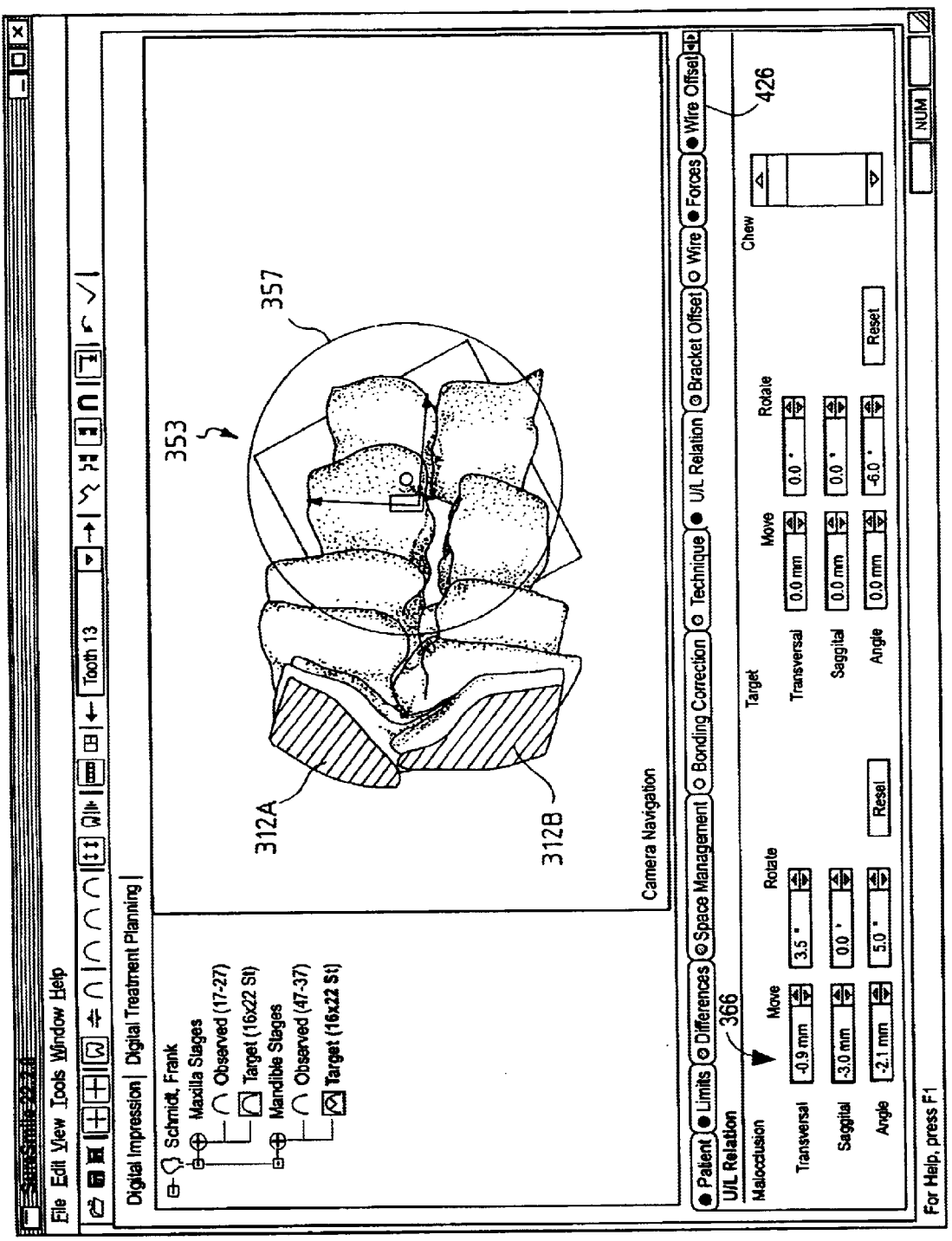
FIG. 17 is a screen shot illustrating of a portion of a target arch, showing a vertical cross-section or clipping plane taken through the teeth. This view is helpful in adjusting the relation between the upper and lower jaw.

The viewing options also include a clipping plane feature by which cross-sections of the teeth through any desired plane are possible. As shown in FIG. 16, the clipping plane is shown through the upper jaw, but the user at can move this plane in three-dimensional space at will. If the teeth are magnified, this clipping plane feature is very useful for inspecting contact points between the upper and lower jaw, viewing and adjusting the upper and lower jaws in the initial bite registration, and adjusting the location of the occlusal plane. For example, in FIG. 17 the clipping plane is shown through the upper and lower incisors 312A and 312B.

The clipping plane is manipulated like an object with the object navigational tools shown in FIG. 11. The plane is accessed using a tools menu and the user highlights or selects SHOW CLIPPING PLANE. A plane appears on the screen. The user then clicks on the object navigation icon 353 (FIG. 10). The object navigational controls 355 of FIG. 11 then are displayed. The user then positions the mouse pointer over the navigational controls 353 to adjust the position of the clipping plane. When they start dragging in the region outside the large circle 357 (FIG. 11, FIG. 16), the plane is turned clockwise or counterclockwise. Then they start dragging inside the large circle 357, the plane is rotated in the direction indicated by the dragging. When they start dragging from inside the small circle 359, the clipping plane is moved in the direction of the dragging. When they start from inside the rectangle 361, if they drag up they cut less into the model, by dragging down they cut further into the model.

Viewing and Adjusting Initial Bite Registration

The first step in typical treatment planning is deciding where to place the teeth in three-dimensional space. This will ordinarily involve a definition or fixation of the vertical level of the teeth relative to the bones, and defining an occlusal plane, and adjusting the occlusal plane sagittally and transversely. This, in turn, will ordinarily involves an assessment of structural relationship between the teeth and the maxilla and mandible. The orthodontist performs this by accessing and studying x-ray, CAT scan, photographs or other two dimensional data stored in the patient records portion of the treatment planning software, and of course the three-dimensional model of the malocclusion, with the teeth either represented as individual tooth objects or in context with the surrounding anatomical tissue. The mid-sagittal profile of the incisors and molars is set up by superimposing the mid-sagittal plane of the teeth over the x-ray.

Figure 9:
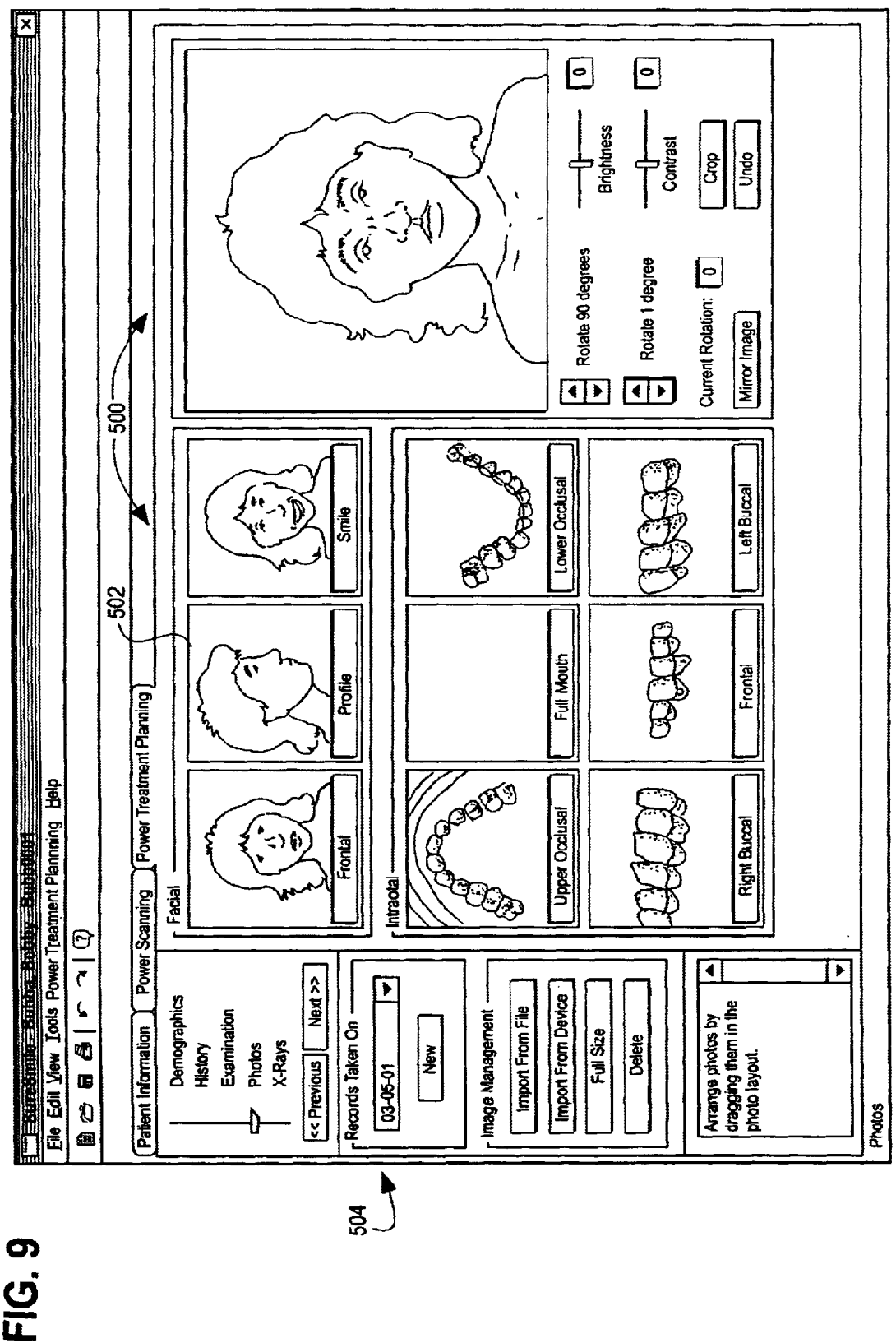
FIG. 9 is a screen shot from the treatment planning software showing some aspects of patient information that are stored in memory and accessed by the software, including photographs, patient information, examination notes, x-rays, medical and/or orthodontic or dental history, and the three-dimensional model of the malocclusion.

FIG. 9 is a screen shot from the workstation running the treatment planning software showing a patient information screen. The screen includes a region 500 for storing various photographs 502 of the patient's head and face, and various views of the patients dentition. The photographs are taken with a digital camera and loaded into the workstation, and accessed from the treatment planning software. The patient information section of the software also includes separate screens for entering and displaying other pertinent information for the patient, accessed through a menu 504. These additional screens (not shown) include the patient demographics, patient medical, dental and orthodontic history, examination notes, and x-rays.

To assist this process, the treatment planning software provides the ability to view and adjust the initial bite registration. The initial bite registration between the upper and lower arches can be modified using the U/L relation tab 327 of FIG. 12. The user can move or rotate the lower jaw relative to the upper jaw by entering values in the field 366. The user can also simulate a chewing motion of the upper and lower jaws by moving the slide bar 368 down. During this simulation the lower jaw moves from side to side and up and down to simulate a chewing motion.

Figure 14:
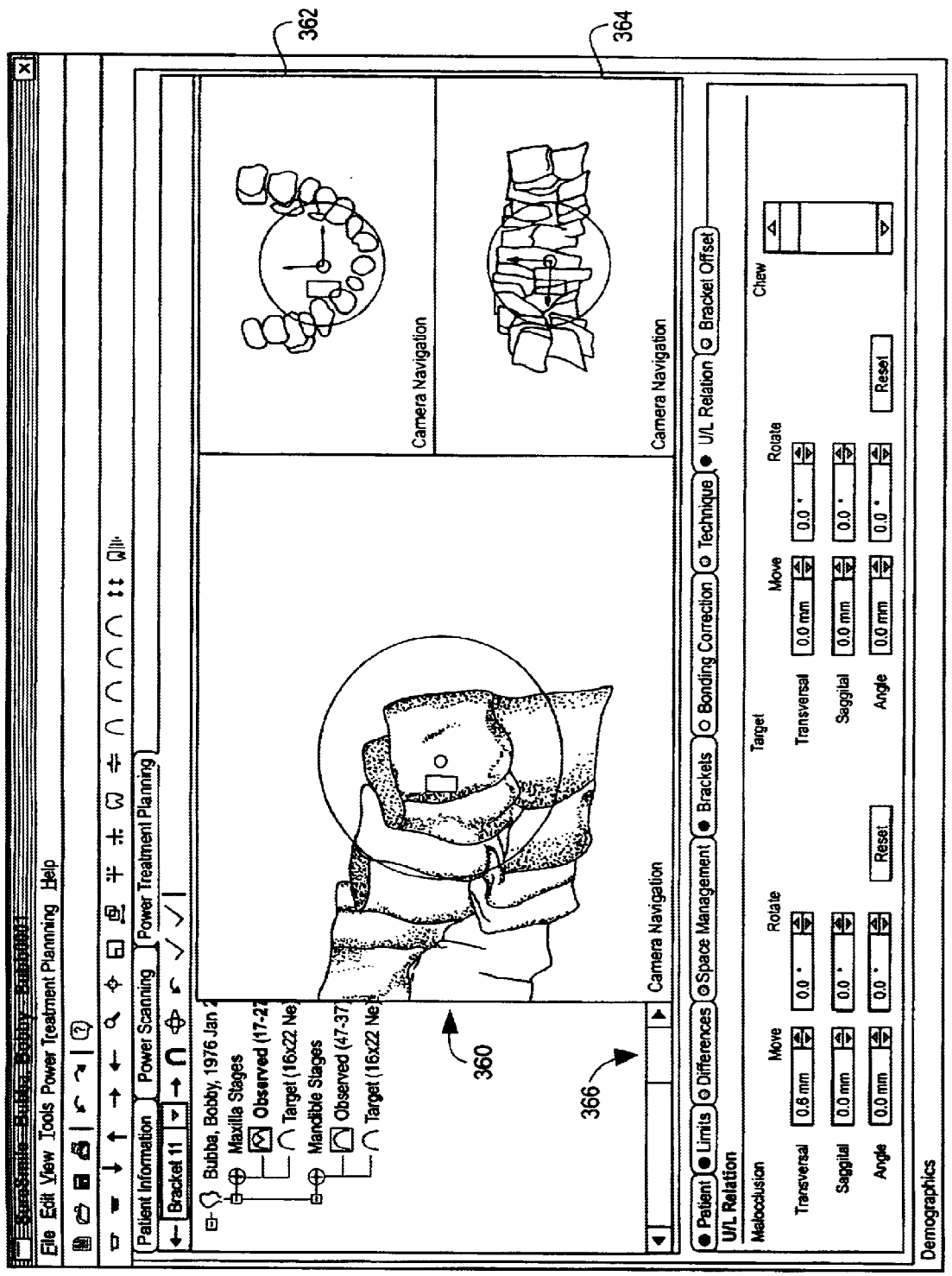
FIG. 14 is another screen shot from the treatment planning software, showing several views of the observed stage and the fields by which an orthodontist can enter values to alter the relation of the upper jaw to the lower jaw as an initial step of planning treatment.

FIG. 14 shows how the three-dimensional viewing area on the screen on the workstation can be broken up into separate screens using known windowpane techniques. Here, in windowpane 360, the area of the molar in the observed stage is displayed, with the orthodontist able to assess the upper and lower relation and change values for the upper and lower relation in three planes of space. Simultaneously, windowpane 362 shows the upper and lower jaws as seen from above. Windowpane 364 shows the dentition looking from the molars out towards the incisors, a view the orthodontist would otherwise not be able to access without the three-dimensional virtual model. These various views, plus the clipping plane tool, and the x-Ray and patient photograph data in the patient records portion of the software, provide a complete suite of tools for effective orthodontic diagnosis, treatment planning, and appliance design, including initial bite registration.

Figure 15:
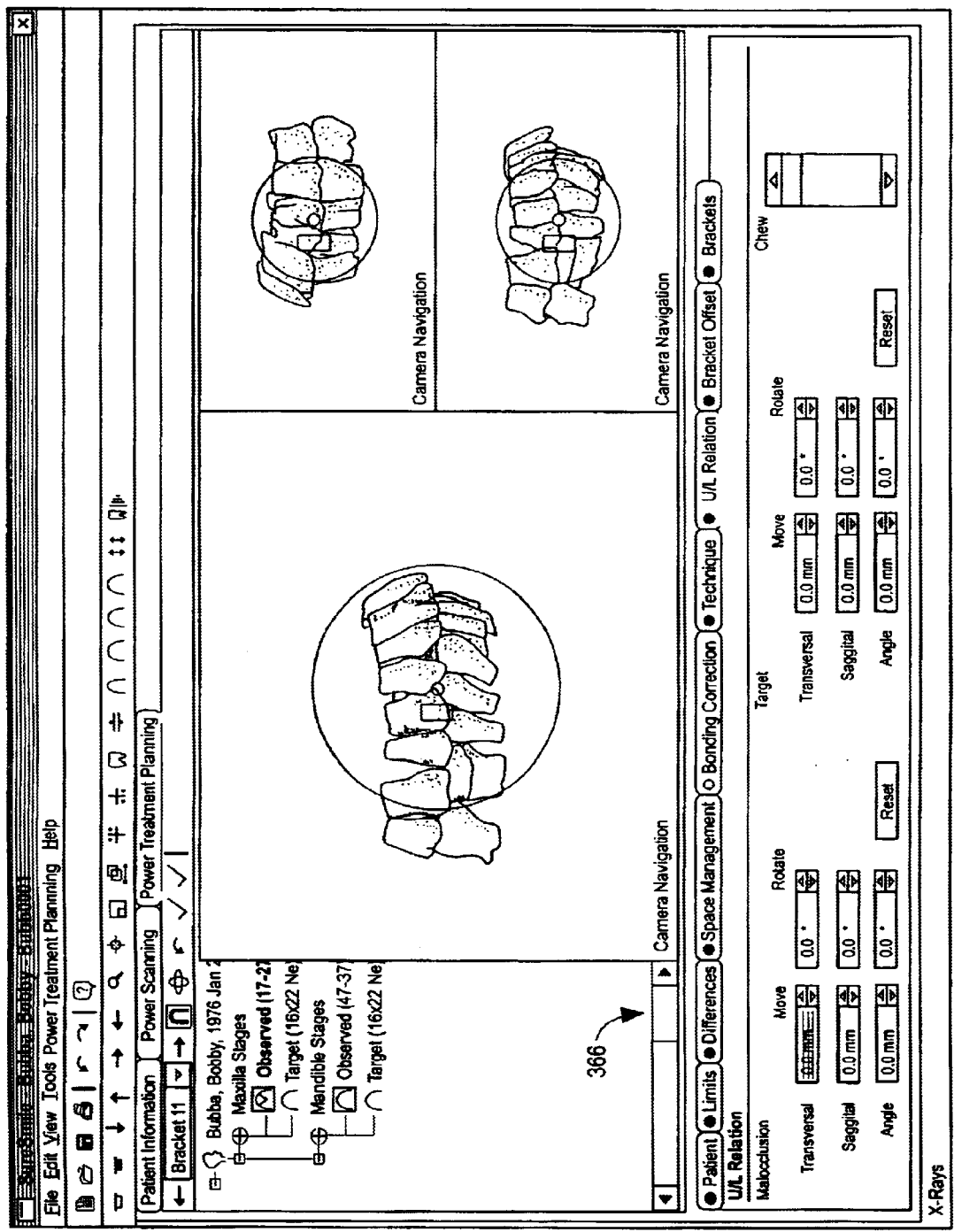
FIG. 15 is another screen shot showing several views of the malocclusion displayed simultaneously, similar to FIG. 14.

FIG. 15 is another screen shot showing the three-dimensional model of the dentition in the observed stage. No values have been entered in the malocclusion field 366 in the U/L Relations tab. By inspection of the upper and lower jaws (using magnification or clipping plane features if needed), the user can set numerical values in field 366 and immediately simulate the corresponding tooth movement to arrive at a desired upper and lower initial bite registration.

Design of Target Archform

Figure 18:
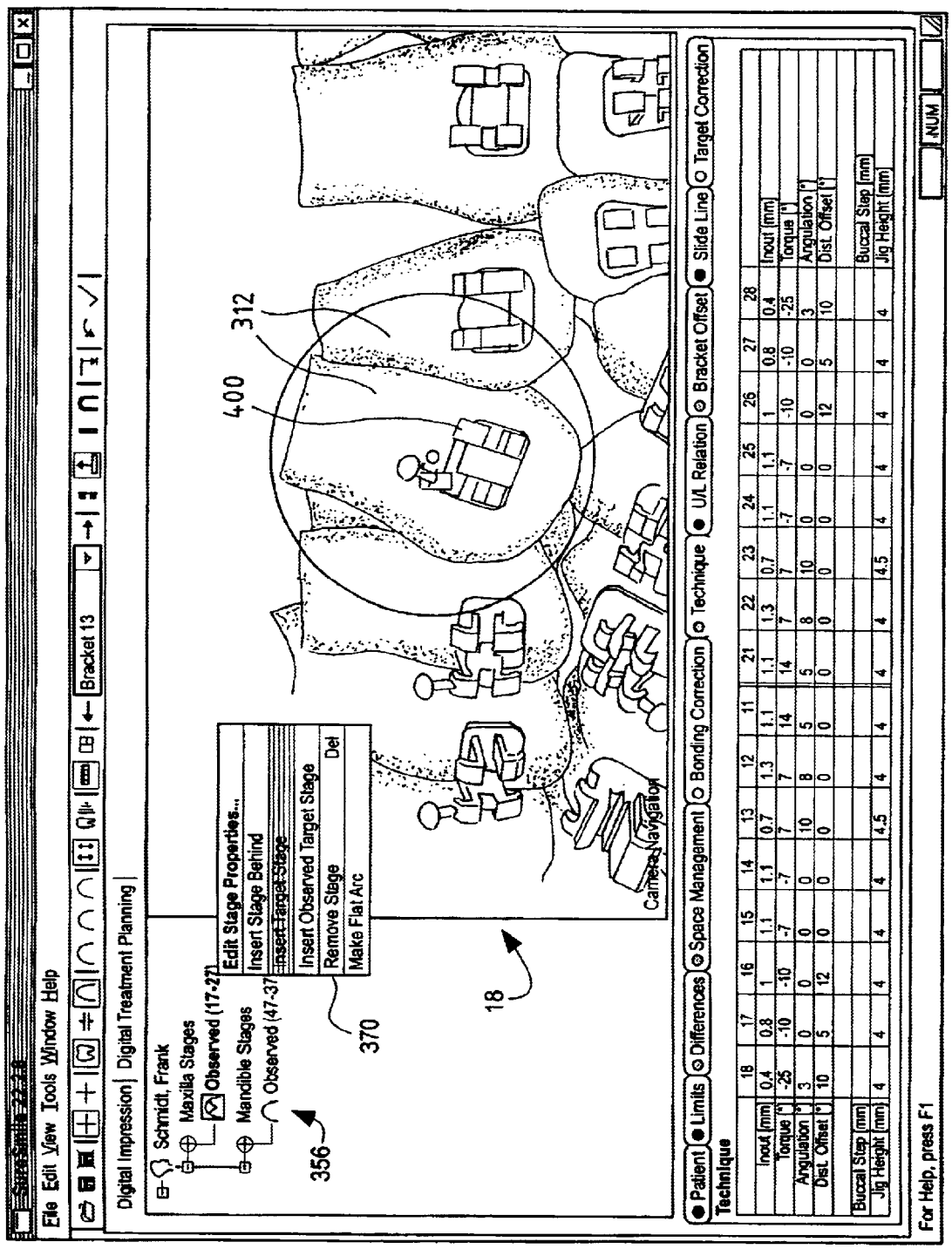
FIG. 18 is a screen shot showing the placement of the virtual brackets on the teeth at the malocclusion, showing the user clicking on an icon to establish an initial archform for the upper arch.

Referring to FIG. 18, after the user has set the initial level of the occlusal plane and inspected the initial observed situation, the next step is selection of a desired or target archform for the patient and the midline. The orthodontist will have previously selected or indicated a general type of archform for the patient, e.g, Roth. The treatment planning software allows the user to generate a target arch based on this archform for the individual patient. The user highlights the observed stage in region 356 and then right clicks the mouse. The pop-up menu 370 appears and the user selects INSERT TARGET STAGE. The target stage is arrived at by creating a flat virtual wire that runs through the virtual bracket slots to create a virtual arch line. The arch shape is based on the user's selected preference for the arch shape, based on the patient's facial anatomy, bone structure, malocclusion, and other parameters using the orthodontist's judgment. The wire target shape has a best fit through the malocclusion bracket slot positions. In one embodiment this wire is flat. It is also possible to design the wire to adapt to the malocclusion in the vertical direction to create a Curve of Spee if desired. The geometry in the transverse direction can also be changed, such as the transverse curve of Monson establishing an inclination of the teeth in the coronal plane.

Figure 19:
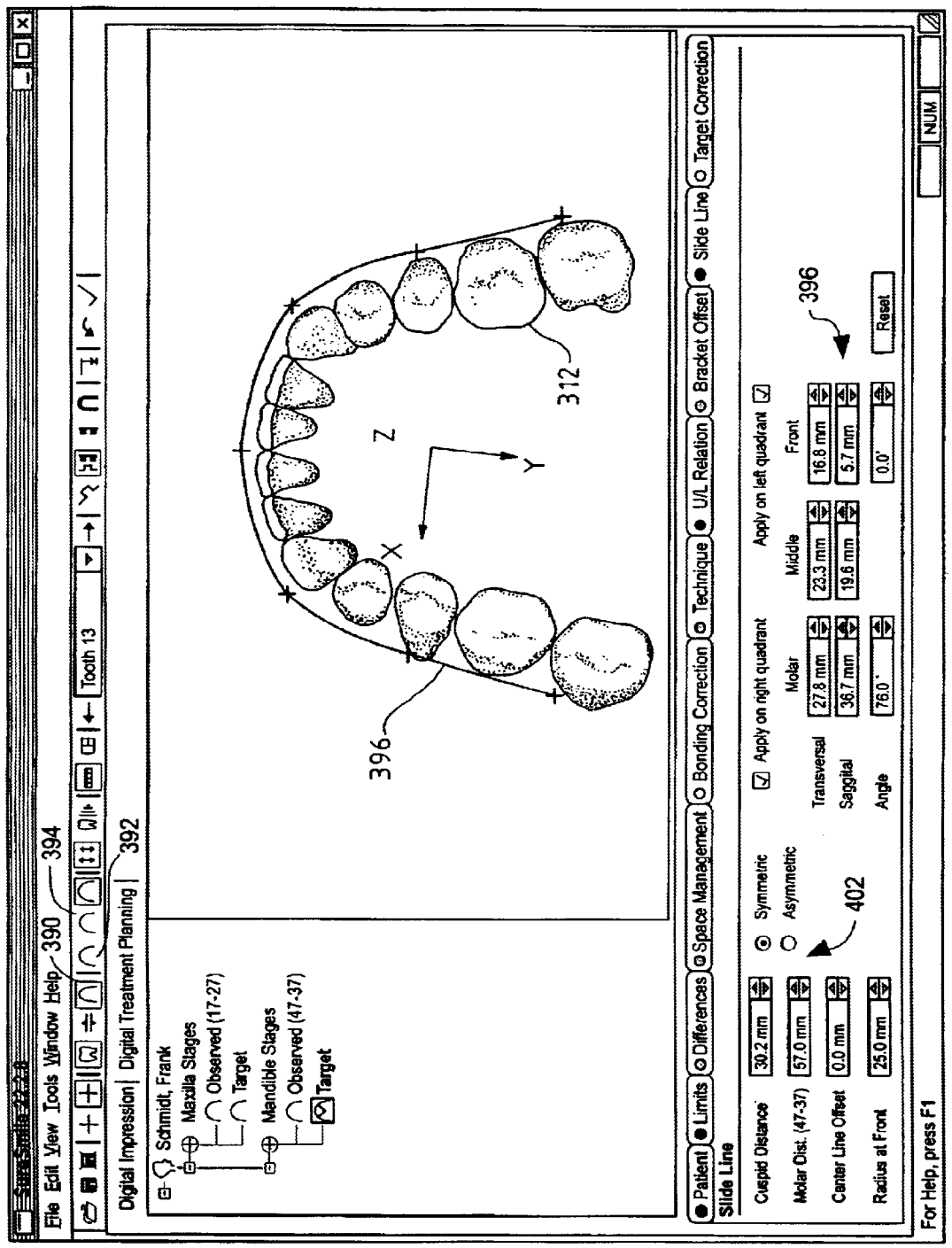
FIG. 19 is a screen shot showing the computer model of the patient's teeth positioned in a target or desired stage, as a result of the user selecting an archform for the patient and the computer placing the teeth along the arch selected by the user.
Figure 20:
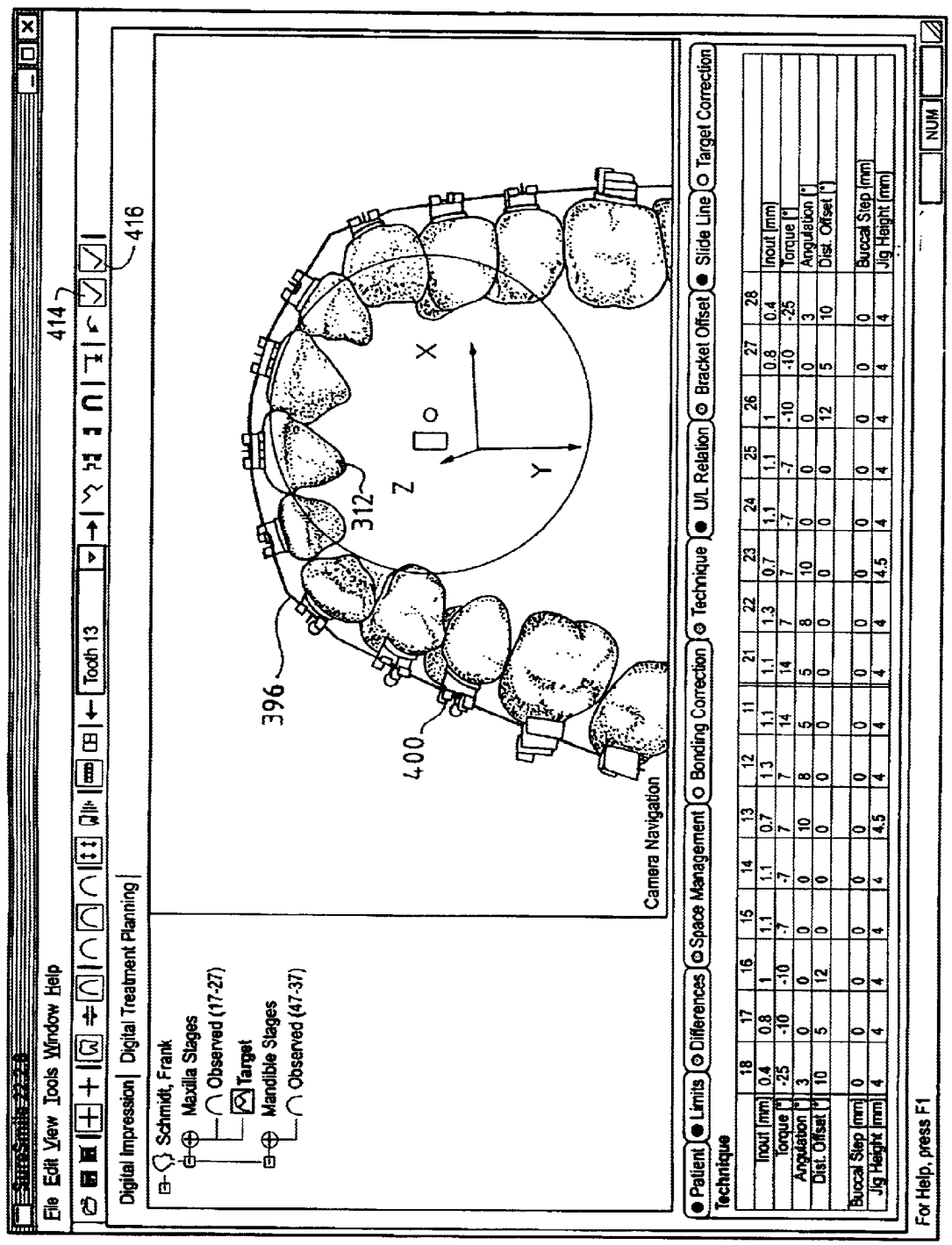
FIG. 20 is another screen shot showing the computer model of the patient's teeth in a target stage, also the brackets and the orthodontic archwire, and showing the numerous parameters available to the orthodontist to customize the tooth position, orientation, angulation, torque, and other parameters on a tooth by tooth basis for the target archform.

FIG. 19 is a screen shot from an orthodontic workstation showing the computer model of the patient's teeth objects 312 positioned in a target or desired condition. The illustration is the result of the user selecting an archform for the patient from a known type of archform and the computer placing the virtual brackets along the arch selected by the user. This is executed by placing or threading the virtual brackets along the archform or curve selected by the orthodontist. The brackets are omitted from FIG. 19, but are shown in FIG. 20. When the initial target archform is created, the slide line tab shown in FIG. 10 is activated.

The initial target archform presented to the user in FIG. 19 is only an initial archform. The treatment planning software allows the orthodontist to change many variables in the target situation, simply by entering new values in the slide line area 402 of the screen display. FIG. 19 shows some of the parameters by which the orthodontist can adjust the shape of the arch, including the distance between the cuspids, the distance between the rear-most molars, the center line offset, and the radius of curvature at the front of the teeth. Slide line area also permits the user to select a symmetrical archforrn or an asymmetrical archform, and apply corrections on the right and left quadrants as indicated. As values are entered in area 402, the shape of the archform is instantaneously modified on the screen display, allowing the user to simulate various potential archform configurations for the patient.

In generating the archforms shown in FIGS. 19 and 20, the user will ordinarily set up the lower arch first. The upper arch is automatically derived from the lower arch. The user can view the arch forms in several ways using three arch icons 390, 392 and 394. The arch icon 390 is for the malocclusion arch, which causes a blue line to appear on the screen which exhibits the curvature of the observed arch or malocclusion. The line passes through the slots on the virtual brackets, as placed on the teeth. The arch icon 392 is for the target arch, which represents a custom archwire passing through the bracket slots of the teeth in the target situation. The line 396 in FIG. 19 represents this arch. The arch icon 394 if for an ideal spline or curve generated by the software to represent an optimal shape. The arch retains a parabolic shape as the user manipulates the target arch using the entries in the slide line. The numerical values in region 398 of the slide line tab represent checkpoints and boundary conditions on the ideal spline associated with the icon 394. These values can be edited as indicated.

Since the software allows for generation and display of a malocclusion archform and a planned archform, the difference between the two archforms indicates the space needed to control arch length inadequacy; i.e., to identify the need for interproximal reduction, extraction, or control of gap size. Interproximal reduction can be achieved by the clipping plane feature, and the simulation of shaping of individual tooth objects in three planes of space. The simulation of extractions and control of gap is provided for as explained later.

Space Management—Management of Extractions and Gaps Between Teeth

Figure 25:
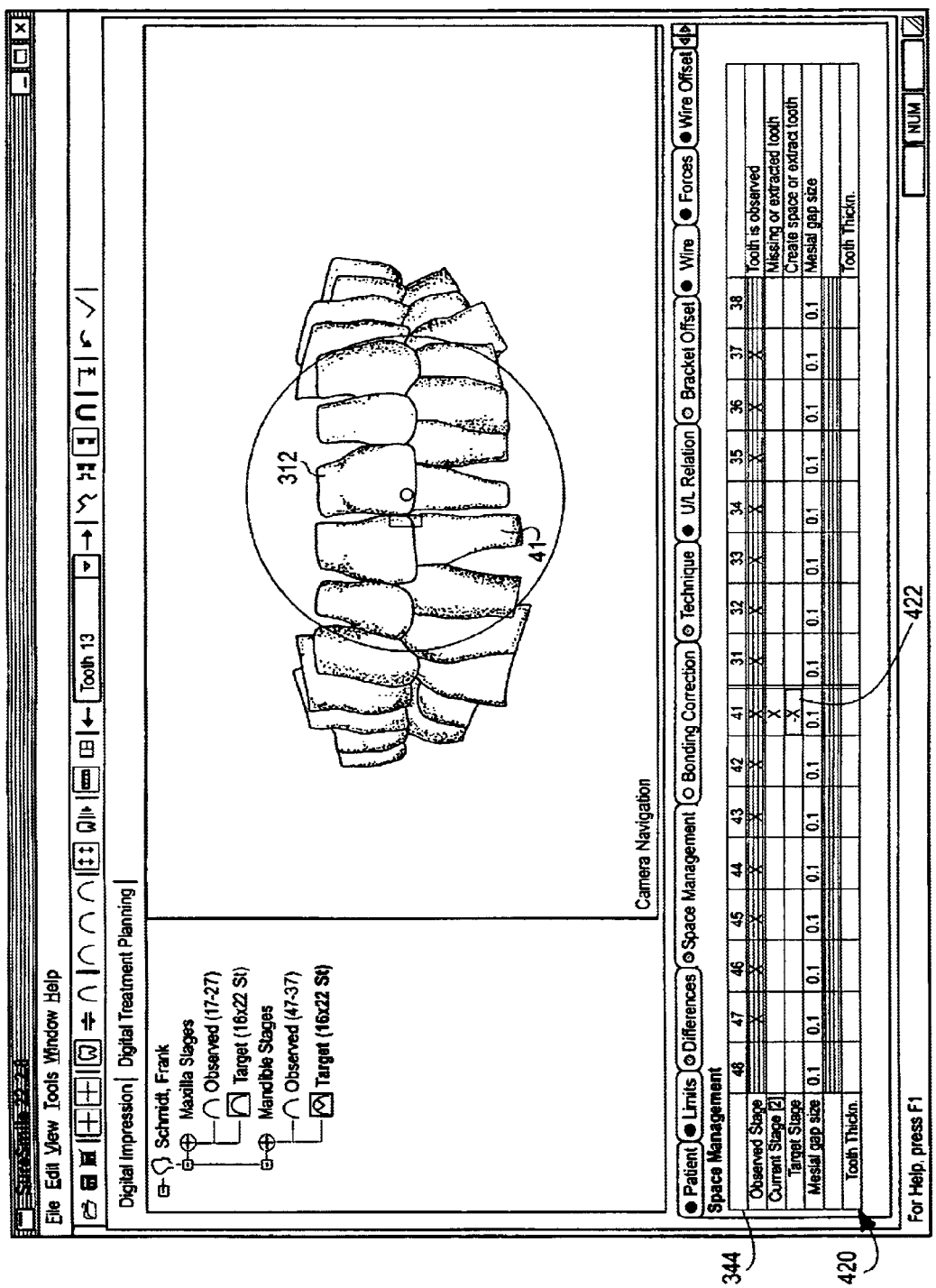
FIG. 25 is another screen shot showing a space management feature by which the target situation can be adjusted by specifying spaces between teeth or by extraction of teeth.
Figure 26:
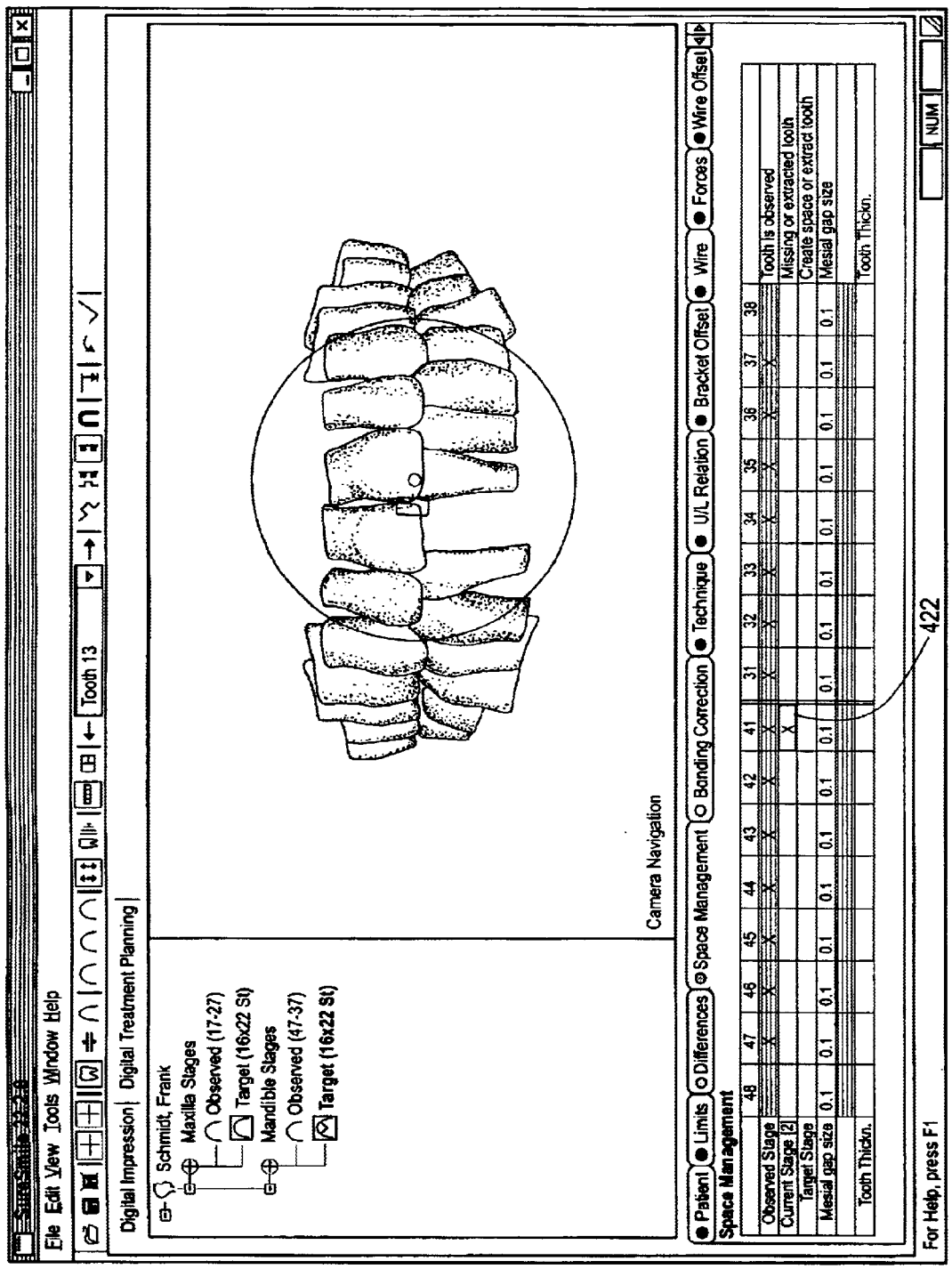
FIG. 26 is a screen shot illustrating the simulation of an extraction of a tooth number 41.
Figure 27:
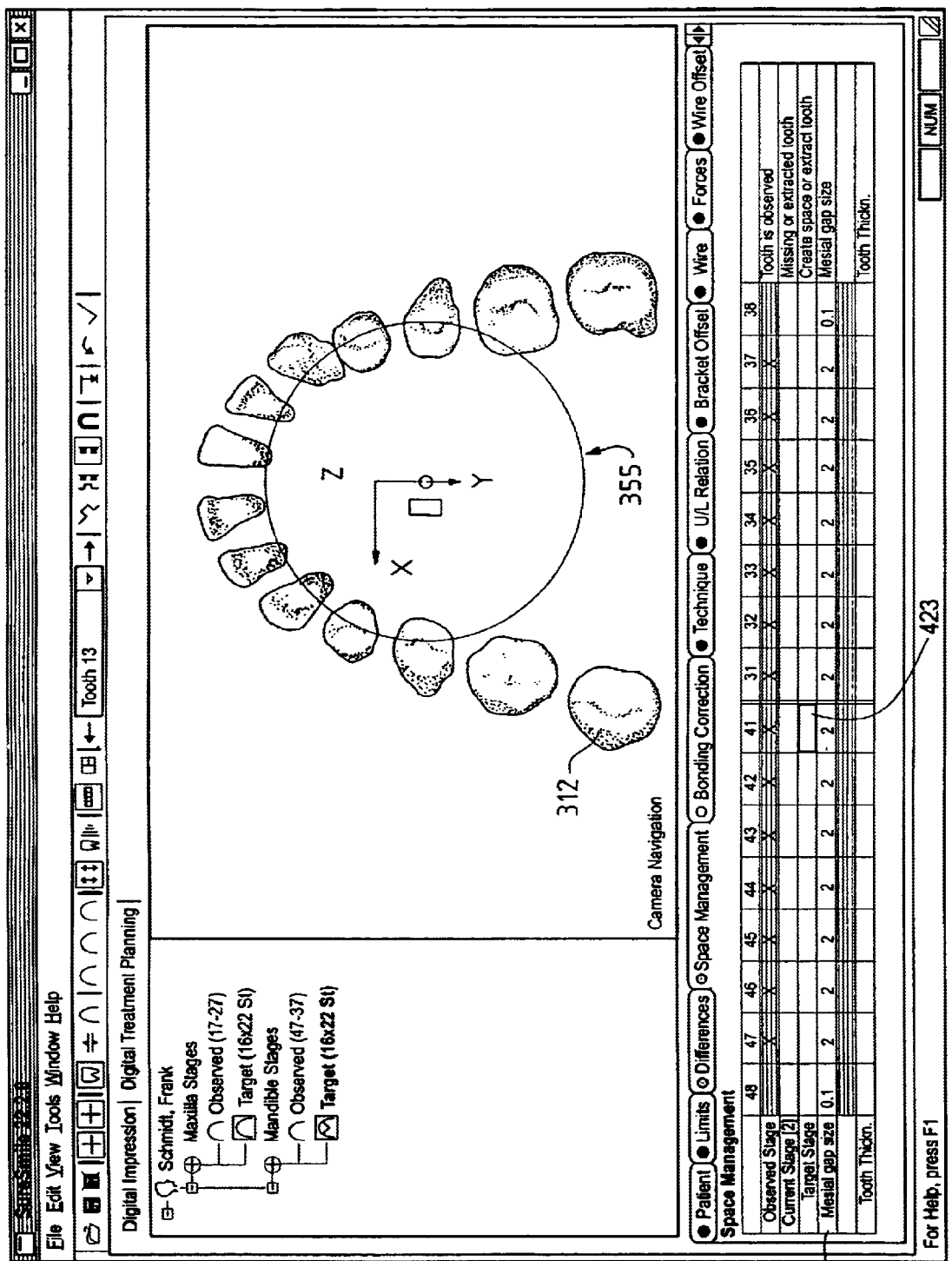
FIG. 27 is a screen shot showing the user modifying the mesial gap between the teeth and showing how the user-specified mesial gap is instantaneously represented on the screen.

The treatment planning software provides a space management tab 344 that is used for managing space between teeth, including tooth extraction. FIG. 25 is a screen shot showing the target situation of both the upper and lower jaws. The user clicks on the space management tab 344, and the region 420 of the tab appears. The region 420 allows the user to simulate the extraction of a tooth in either the current or target stage. Here the user is simulating the extraction of tooth number 41 by clicking on the appropriate cell for that tooth in the rows for current and target stages. The result is shown in FIG. 26. The extraction of tooth 41 is simulated. The region 422 also allows the user to enter values for the mesial gap size between teeth. A default value of 0.1 mm is provided. However, the user can change these values. For example, the user can enter any values in the row of cells for mesial gap size as shown in FIG. 27 (in this example 2 mm). Note also in FIG. 27 that the simulation of the extraction of tooth 41 is not being performed since the cell 423 is not checked. The tooth moves distally if a positive number is typed in the cell for that tooth in the mesial gap size row 424. If a negative number is typed into the cell, the tooth moves mesially.

Adjusting Virtual Bracket Position

After the upper and lower archforms have been optimized, the user may wish to adjust the position of the virtual brackets 400 on the teeth. The step of adjusting the virtual bracket position can also be performed prior to the design of the archform.

The vertical position of the virtual brackets relative to the incisal edge of the virtual teeth is one adjustment that can be made. This distance can be measured using the measurement tool described earlier. Bracket manufacturers have recommendations for this distance. If the initial landmarking has placed the brackets outside of the recommended distance, this distance can be adjusted by using the object navigational tools. Alternatively, the user can select preferred values for the archform and the bracket set (bracket manufacture, bracket technique and wire type, e.g., straight) and the landmarks and virtual brackets will be placed on the teeth at the recommended distance.

The bracket placement can also be performed interactively by the user. The user looks at every tooth 312 one by one (using a screen such as the screen shot of FIG. 18) to see if they are basically satisfied with the bracket 400 position, e.g., angulation, side to side position, and its relation to teeth in the opposing jaw. The user may be performing this step while viewing the malocclusion, or the target stage. To improve the position of the virtual bracket 400, the user selects the bracket, zooms in if necessary, and adjusts the position of the bracket on the tooth surface using the navigational tools as described earlier.

Correction of Individual Tooth Position In Target Archform

Figure 21:
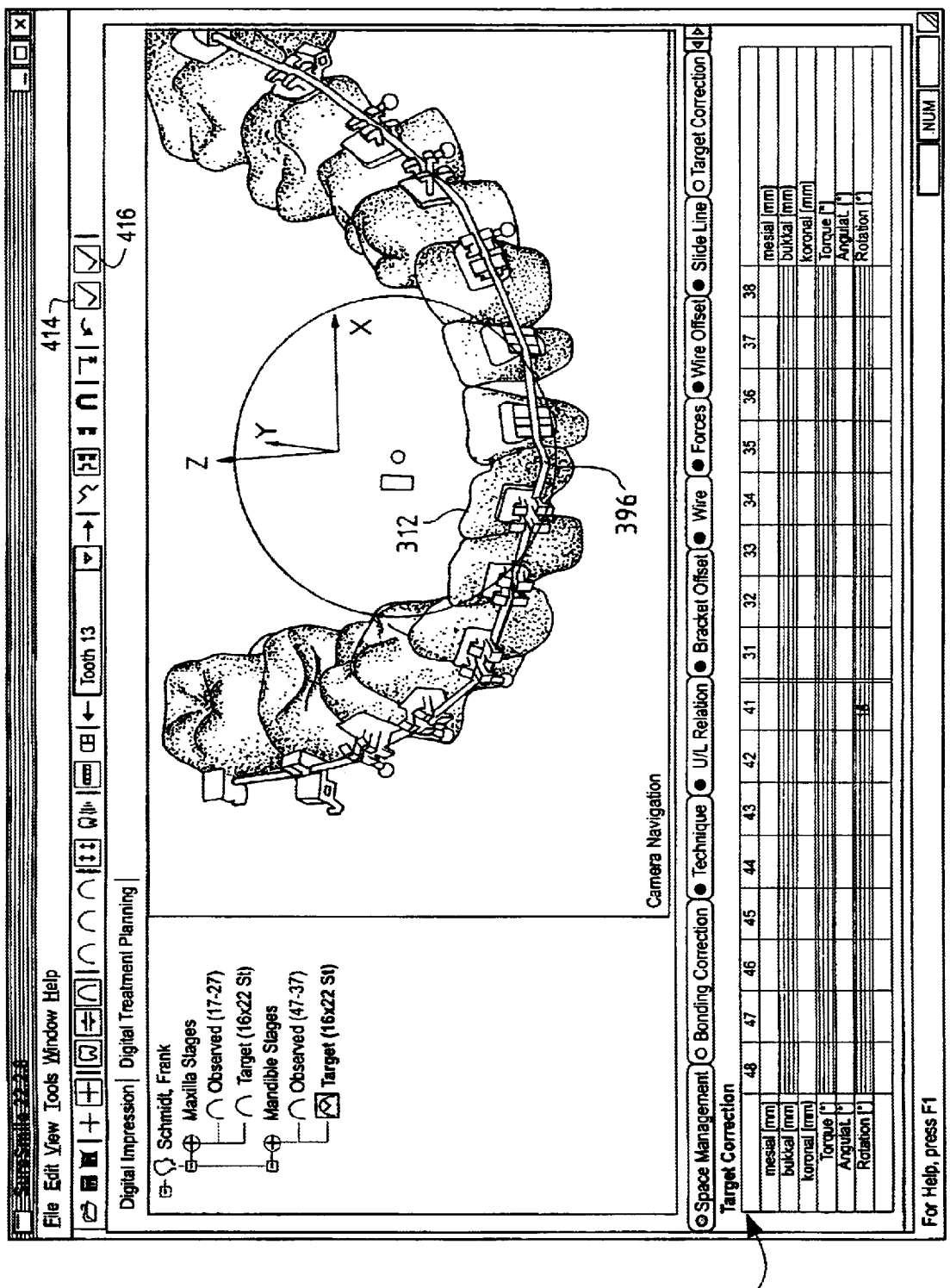
FIG. 21 is another screen shot showing a view of the target situation, with brackets and archwire, showing fields allowing the orthodontist to moving the teeth objects relative to each other in planning treatment for the patient.
Figure 24:
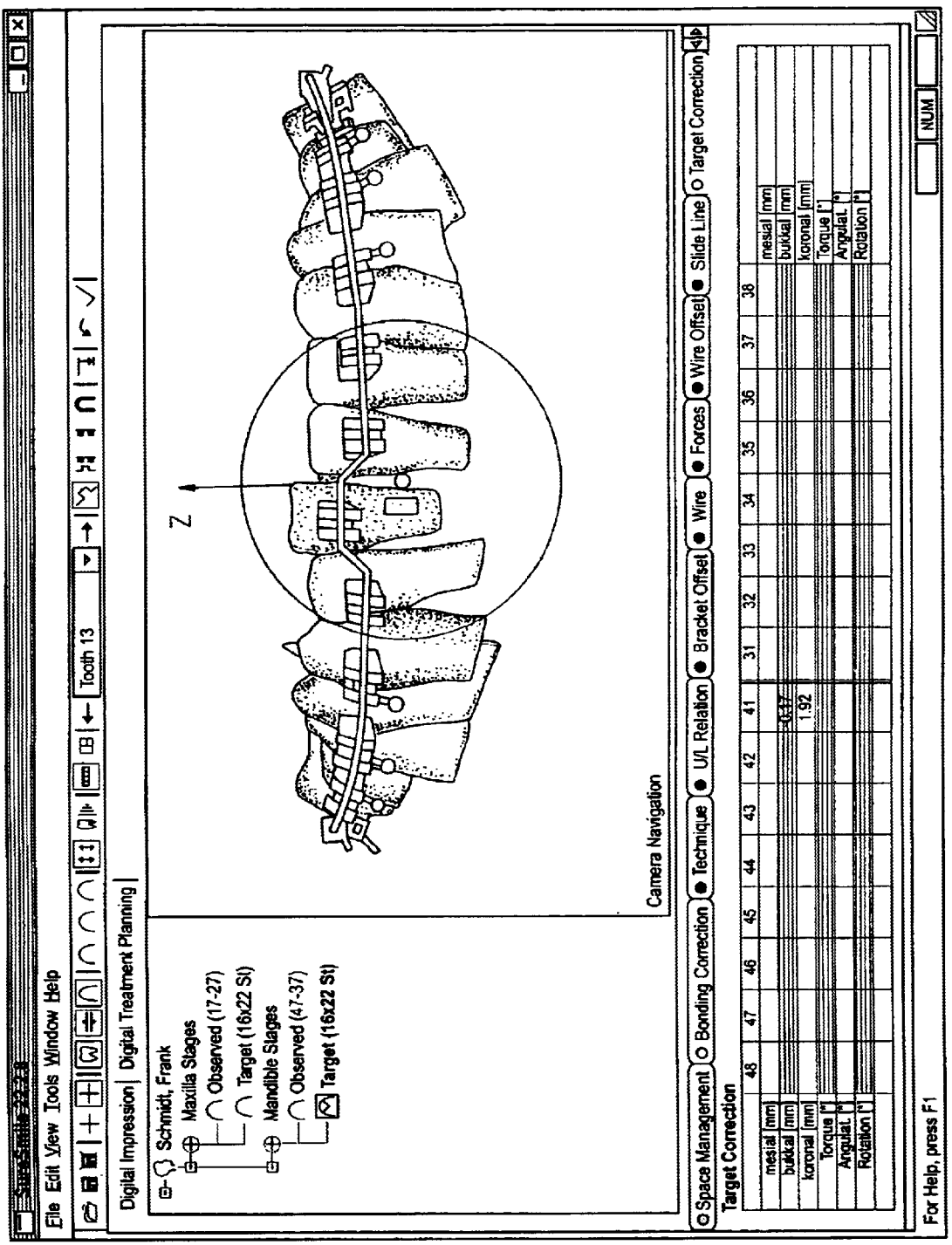
FIG. 24 is another screen show showing the target stage, with the brackets and archwire, showing a tooth moved in the buccal and coronal directions by an amount indicated by the orthodontist, and the correction incorporated into the archwire.

After the archform has been designed and the bracket placement optimized, the user can adjust the individual tooth position on a tooth by tooth basis in the target arch. There are three ways this can be performed. First, the user can use the tables in the Target Correction tab. See, for example, FIG. 21, in which the user has entered a value of –15 degrees for rotation of tooth number 41, and the tooth is rotated by that amount. The correction is realized by a bend in the archwire 396. The bracket position on the tooth does not change in this example. The target corrections tab 410 permits any values to be entered for mesial, buccal and coronal translation in three planes of space, and torque, angulation and rotation movements about three orthogonal axis. Thus, independent tooth position corrections are available in 6 degrees of freedom for every tooth, merely by entering values in the tables in the target corrections tab 410. Another example is shown in FIG. 24, in which a new target position is shown for tooth number 41.

Figure 28:
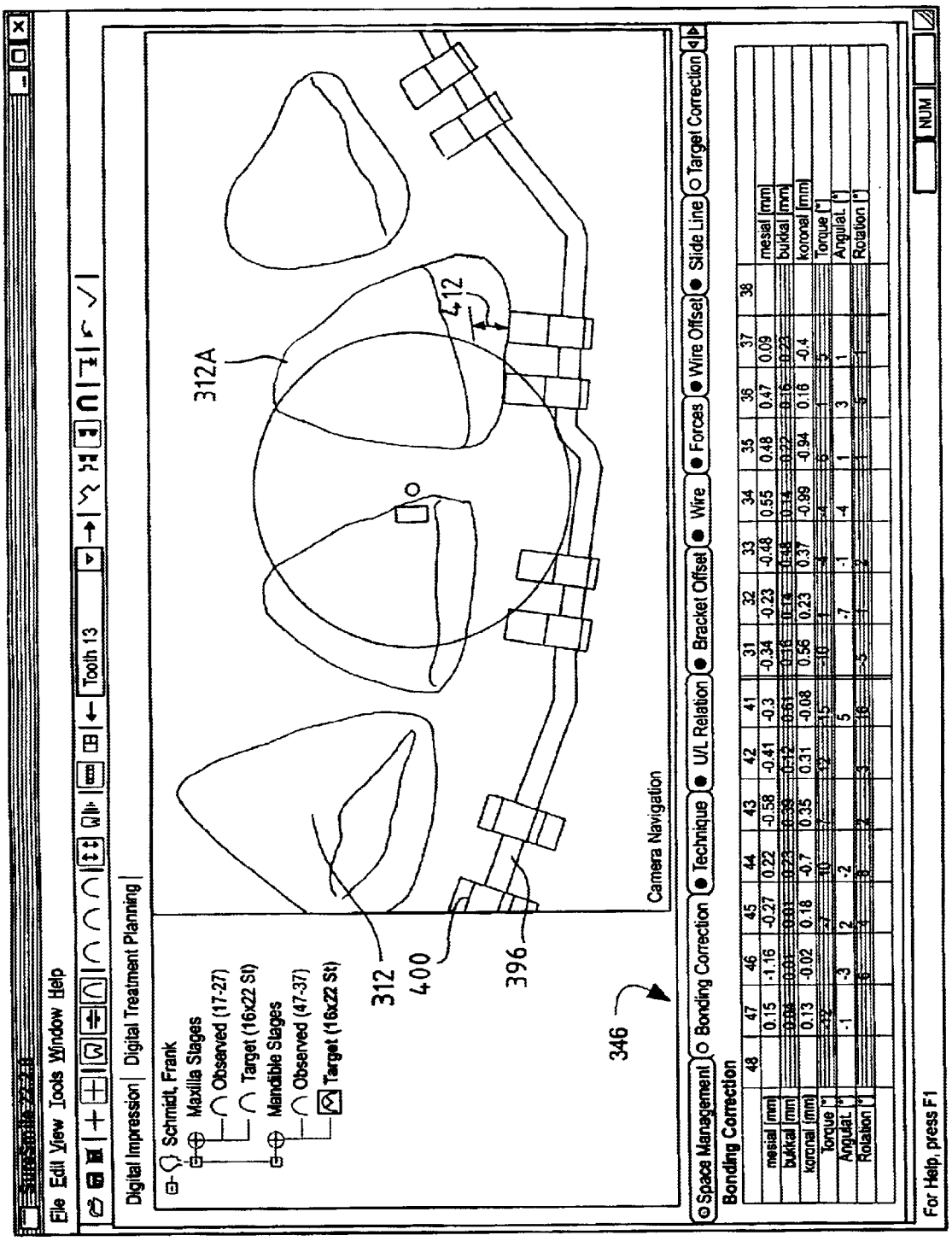
FIG. 28 is a screen shot showing the user modifying tooth position in a target stage on a tooth by tooth basis using a bonding correction feature.

Secondly, the user can move teeth using the Bonding Corrections tab 346 of FIG. 12. An example is shown in FIG. 28. The bonding corrections tab 346 allow the user to enter new values for tooth position for any tooth in the arch by merely entering values in the appropriate cell. The selected tooth 312A (tooth number 41) is moved as indicated (here, a new rotation value of –16 degrees is entered). The virtual bracket remains in the same location in space and the gap 412 between the pad of the bracket and the surface of the tooth is taken up by a bonding adhesive when the bracket is bonded to the tooth.

Examples of common tooth movements that can be simulated using the bonding corrections tab or the target corrections tab are moving the lower incisors buccally or lingually, inclining the incisors axially, and leveling the incisors.

Thirdly, the user can simulate tooth position corrections interactively using the navigational tools. The user displays a target stage as needed. A tooth object is selected as explained above. The user clicks on the zoom icon 341 of FIG. 10 to zoom in or out as needed. The user then clicks on the object navigation icon 353 to display the object navigation controls. The user then uses the navigation controls to move the tooth as desired. The movement of the tooth is recorded as new values in the bonding correction and target correction tables, in case the user wants to quantify the movement or use those tables for further modification of the tooth position. After the user has moved the tooth to the new position, they click one of two check mark icons 414, 416 (FIG. 20, 21) that are highlighted on the screen. The blue check mark 414 realized the new tooth position via a bonding correction. The red check mark 416 realizes the new tooth position via a wire correction.

Figure 22:
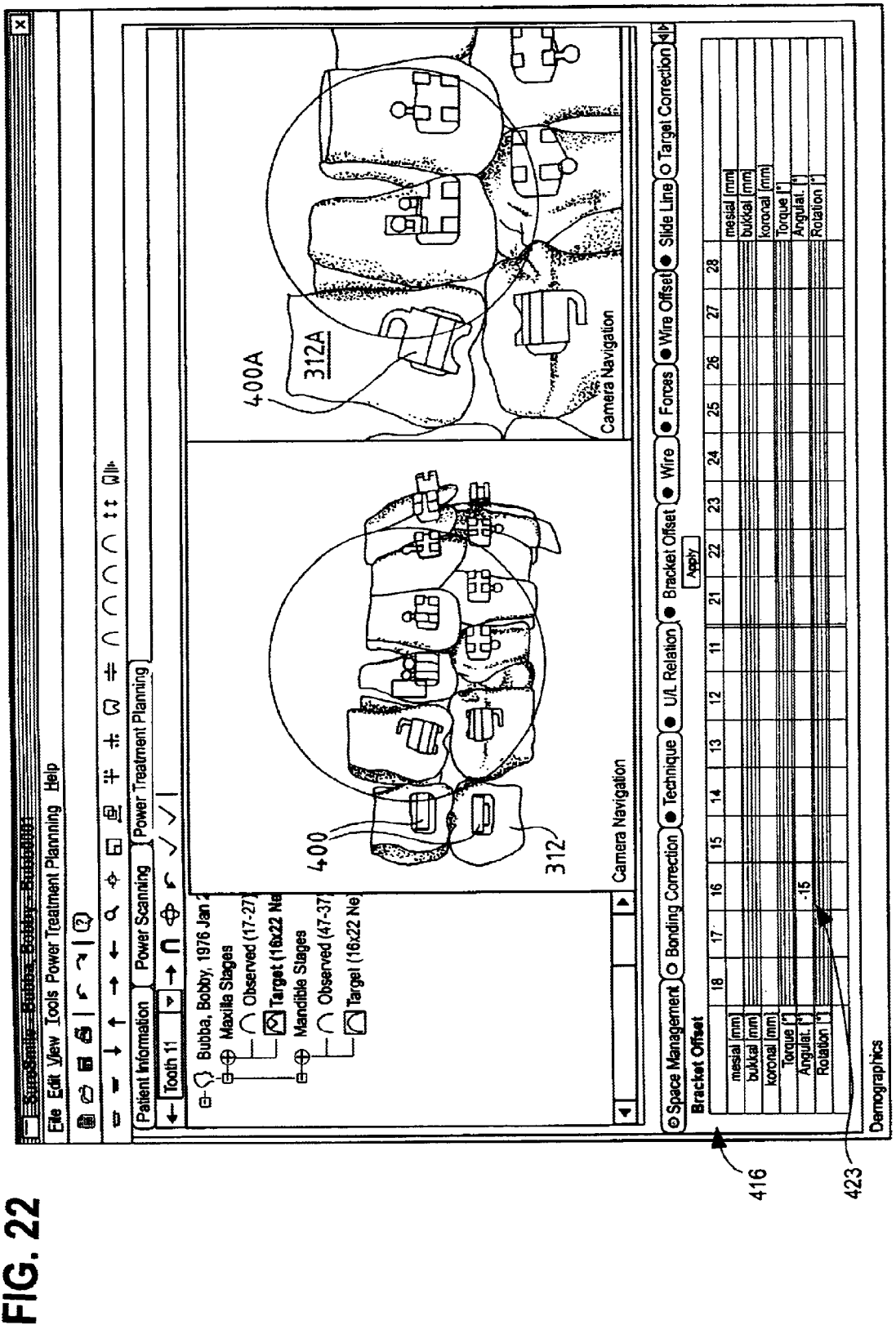
FIG. 22 is a screen show showing a bracket offset correction being entered to move tooth number 16 into an improved occlusal relationship with the opposing jaw.
Figure 23:
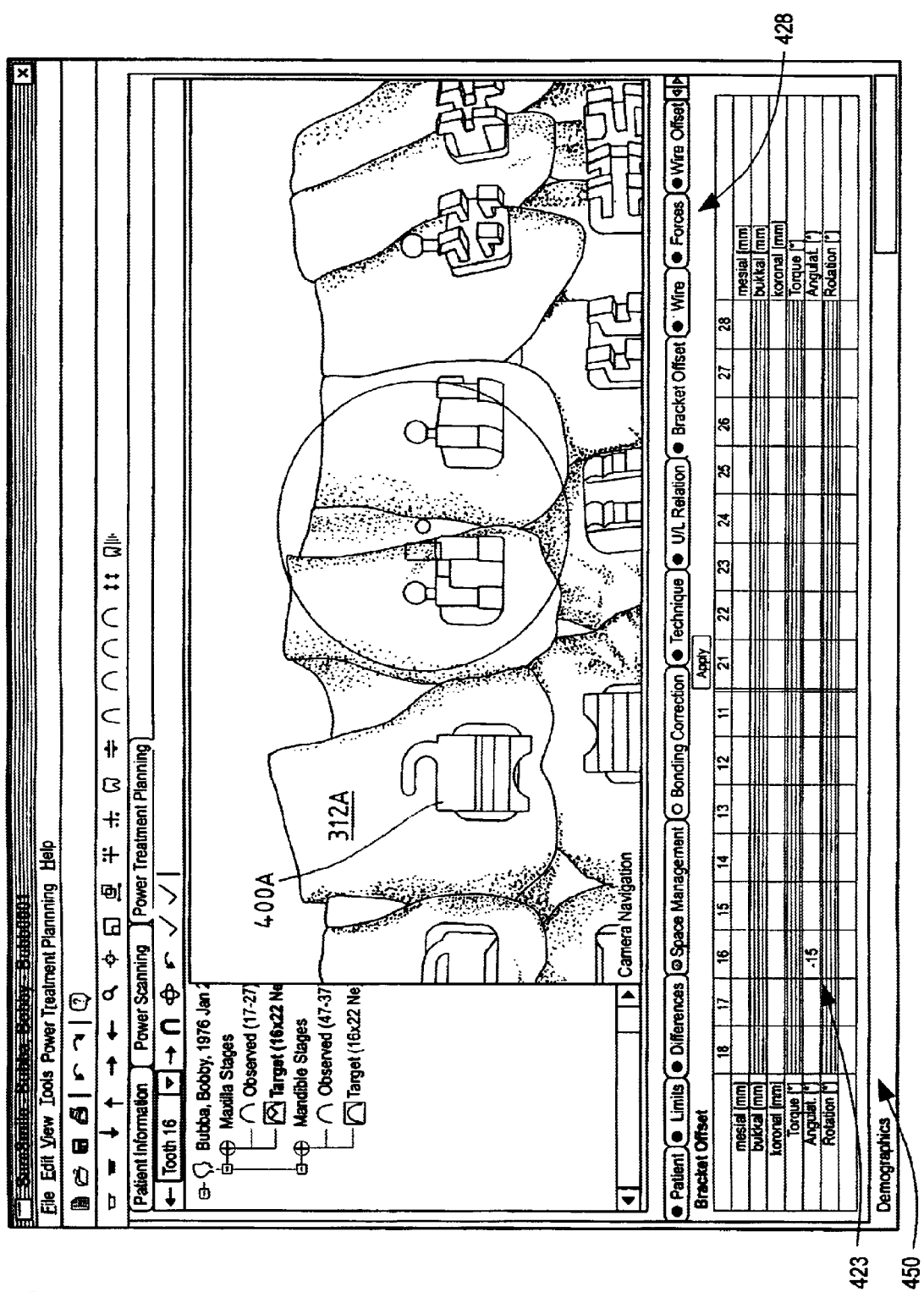
FIG. 23 is a screen shot showing the tooth movement that occurs with tooth number 16 when the bracket offset correction is made.

Another example of correction of individual tooth position is shown in FIGS. 22 and 23. In FIG. 23, the target situation is shown, both with the virtual tooth objects 312 and the virtual brackets 400. Note that with tooth 16 (312A), there is a gap between the rearmost cusp of the tooth and the opposing tooth. The orthodontist can correct this gap by building in a bracket offset, basically repositioning the location of the bracket 400 on the tooth 312A by entering an amount in the table 450 in the angulation cell for tooth number 16 (here −15 degrees). The result is shown in FIG. 23. The change in the angulation value causes tooth number 16 to rotate back into a more desirable occlusion with the opposing tooth.

Wire Tab

Figure 29:
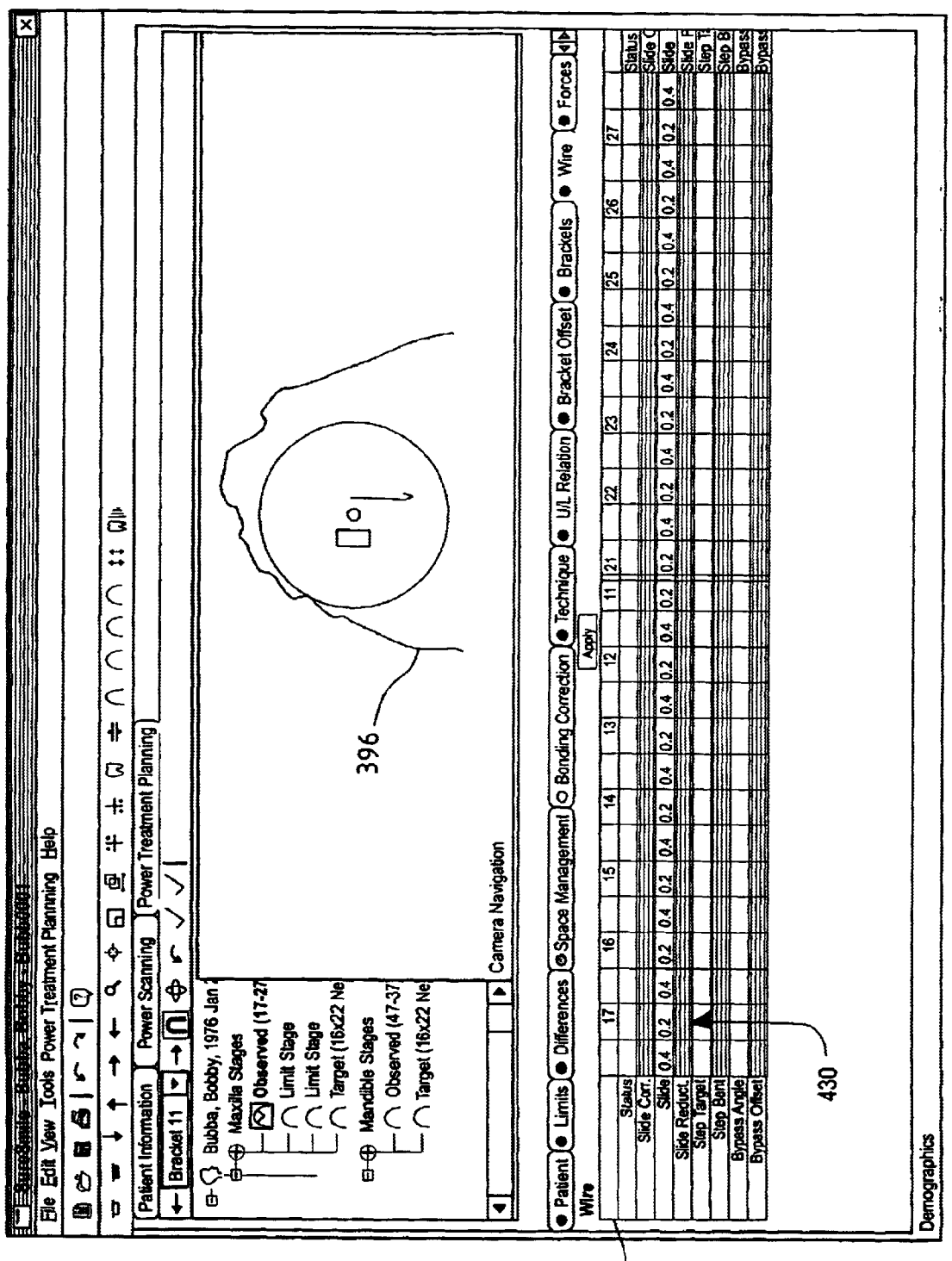
FIG. 29 is a screen shot showing a wire tab, which allows the user to make changes in the shape of an archwire without changing bracket position.

The wire tab 432 of FIG. 29 allows the user to make wire configuration changes, while not changing bracket position. Note that in FIG. 29, the virtual wire 396 is shown isolated from the teeth and brackets. The virtual wire can be scaled to actual size and printed out and provide a template for a manual bending of a wire if the orthodontist chooses not to obtain a wire from the precision appliance manufacturing center. The tab includes a section 430 where the user can view the distance in mm in which the wire will slide relative to the brackets, on a tooth-by-tooth basis, when the teeth are moved from the current situation to the target situation. Note that a collision is detected for tooth 22 in movement of the tooth from the current situation to the target situation. This can be resolved in several possible ways in accordance with the teachings of U.S. Pat. No. 6,250,918 to Sachdeva et al., the contents of which are incorporated by reference herein.

Additional Wire Bending Corrections

Figure 30:
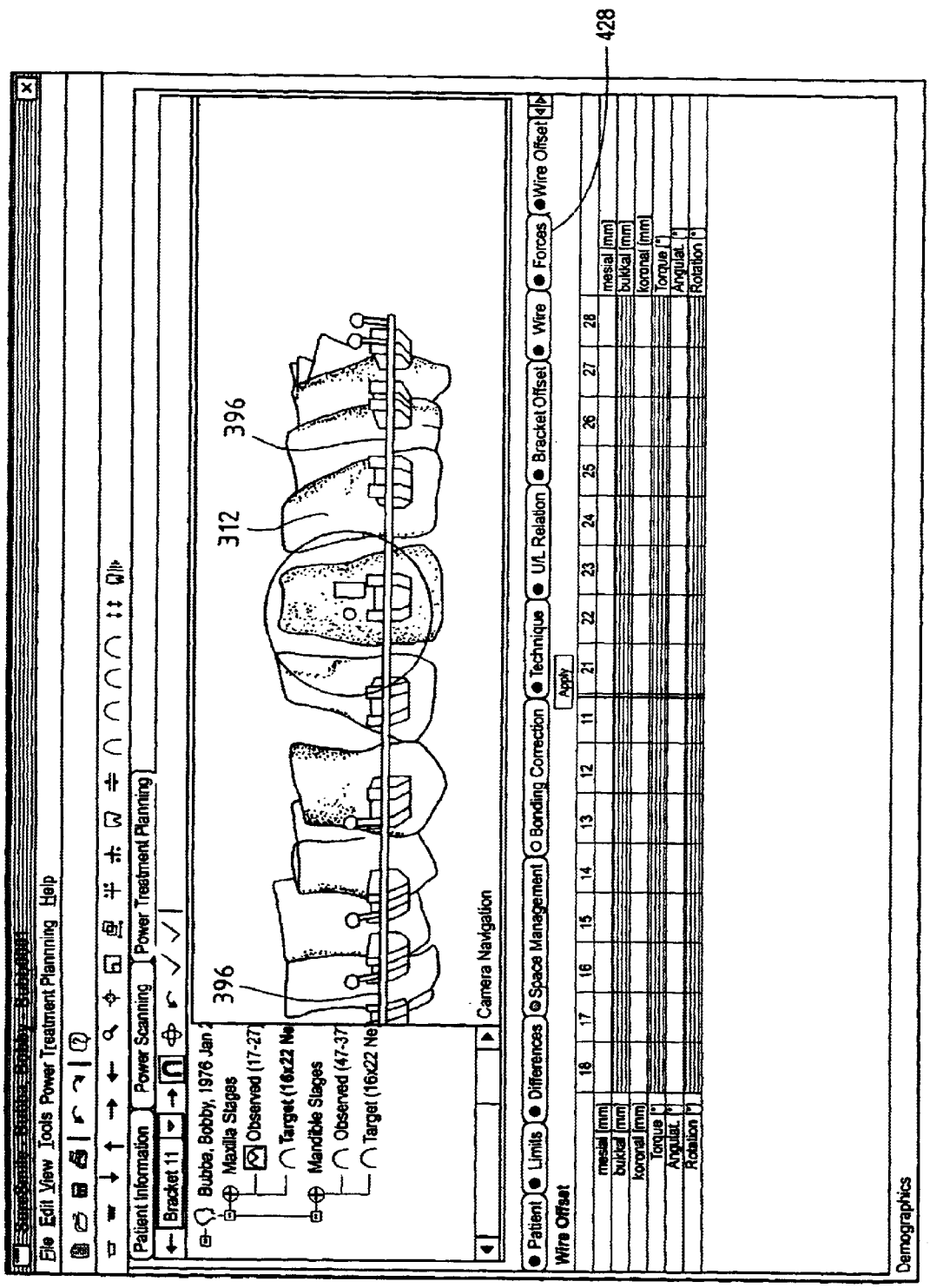
FIG. 30 is a screen shot showing a wire offset tab, which allows the user to change thte the bend size, location, etc., in the wire.

The wire offsets tab 426 (see FIG. 16 and FIG. 30) allows the user to simulate bending a wire 396 to the corrected tooth position while simultaneously retaining the original bracket position. Note that in FIG. 30 the wire 396 is flat with no corrections indicated. The user highlights one of the teeth in the virtual model and enters new values for tooth position. The change is reflected in a new shape for the wire 396. The tab also allows the user to build in over/under compensation into the archwire. These settings do not affect the bracket position. The characteristics of the wire bends, such as the radius of curvature, can be controlled by accessing a slidings tab (not shown). Another tab, forces 428, displays approximations of the forces the wire applies to each tooth to displace it from its initial position to the target position.

Treatment Stages

Since the difference between the current situation and the target situation is quantifiable in terms of millimeters of movement or degrees of rotation about three axes, the treatment for the patient can be broken up into segments or stages with each stage defined arbitrarily. For example, the orthodontist can specify a first treatment stage as the movement of the teeth from the initial position half-way to the final position. The software includes a screen that permits the user to view the position of the teeth when moved to the half-way position. Basically, the simulation simply multiplies the differences in tooth position between initial and target stages by 0.5 and the resulting tooth positions are displayed on the workstation. Additionally, the user can specify further intermediate positions, such as one fourth or three fourths. With this feature, the orthodontist can monitor treatment and compare the progress of the treatment with the limits or stages that have been set. When the patient comes in for a visit during treatment, the patient's dentition is scanned. The three-dimensional model of the now current situation is compared with the defined stages and perhaps with the target situation. Difference between actual progress and the planned treatment can be quantified. Changes to the archwire can be designed using the treatment planning software to move the teeth in the desired direction to account for unexpected biological influences that may be observed.

The above description of treatment planning has been predicated on the use of a three-dimensional model of the dentition from the scanner, obtained as described above. However, it is possible to perform digital treatment planning by importing into the software three-dimensional software from other sources. Is it known today that three-dimensional models can be exchanged with different software programs in different file formats, similar to the translation programs that convert text documents from one type of file (e.g., Microsoft Word to WordPerfect). Most three-dimensional applications have several import filters for different 3D formats.

However, there are generally two different ways to describe three-dimensional objects: by surface representations and by solid representations. A 3D file that holds 3D data in a surface description consists typically of triangles that form the surface of the object. The STL format is one of the oldest and therefore most common formats that uses triangles. It is used to feed information to stereolithography machines. A more detailed description of STL can be found at http://www.mmsonline.com/artciles.019704.html, the contents of which are incorporated by reference herein.

Treatment Monitoring

Interactive, computer-based treatment monitoring is a significant advantage provided the treatment planning and appliance design aspects of the system described herein. Typically, when the patient comes into to the office during treatment, they will be scanned and a new digital model of the dentition is acquired. From this new model, differences can be monitored between the current situation and the original malocclusion, and differences between the current situation and the target situation or pre-defined limits or treatment stages as defined earlier. These differences can be quantified with precision. For example, a point on the tooth in the current model is selected, and the model of the tooth at the original malocclusion is overlaid on the screen. The superposition of the two teeth allows the user to view the change in position that has occurred. The measurement marker features described earlier allow the user to quantify precisely the amount of movement.

Any deviations between the therapeutic result that is observed and the expected result can be captured precisely and at an early stage in treatment using the scanning and treatment planning features described herein, and corrected for. For example, the orthodontist may need to place additional bends in the archwire. Such additional bends can be performed by simulating the wire shape on the screen, displaying the wire only on the screen, and printing out the screen and using it as a template for bending the wire. The current situation could also be forwarded to the precision appliance center for manufacture of a new appliance. Of course, these monitoring and treatment corrections are applicable to any type of appliance selected for the patient.

Appliance Manufacturing

The appliance that is manufactured in accordance with the treatment planned for the patient can vary within the scope of the invention and will depend on the application, including the type of appliance desired by the orthodontist and the patient. Obviously, the treatment planning and simulation features described above can be used in wide variety of treatment regimes, including flat wires and brackets, finishing wires, retainers, Herbst devices, expansion devices, and removable, transparent aligning devices such as those furnished by Align Technologies. For example, the movement of the teeth from the current or observed stage to the target or treatment stage can be broken into a series of movement steps. For each step in the process, the position of the teeth in that stage is known by virtue of the manipulation of the individual tooth models in the treatment planning software. These tooth positions can be used to manufacture the aligning devices.

In a representative embodiment, the results of the treatment planning software are used to generate a customized orthodontic archwire and a bracket placement tray for precise placement of off-the-shelf brackets onto the patient's teeth. When the treatment planning features have been executed to the satisfaction of the orthodontist and the proposed target situation finalized, the treatment planning software will store the following information (in addition to the patient records):

1) the virtual model of the current stage or malocclusion;
2) the placement location of the brackets on the malocclusion, including the type and dimensions of the brackets;
3) the orthodontist's selection of a type of archwire (including material and size); and
4) the target situation, including the location of the teeth and brackets in three dimensions at the target situation.

Note that it is not absolutely necessary for the appliance manufacturing step to calculate or even know the shape of the archwire. Archwire geometry is dictated by bracket positions in three-dimensional space when the teeth are in the target situation. This bracket position information is included in the target situation, no. 4) above.

With reference again to FIG. 1, the above information from the treatment planning software is sent over a suitable communications medium 24 in digital form to the precision appliance service center 26. The service center manufactures a customized archwire and a bracket placement tray for placement of the brackets at the intended location on the teeth in the malocclusion.

Basically, the position of the bracket slots, and the shape of the brackets, when the teeth are in a target situation, is information that is ultimately developed and stored by the treatment planning software. This position of the bracket slots and the shape of the slot (e.g., the length) is of course known in three dimensions. From the slot shape, it is possible to derive a three-dimensional set of line segments that represent the shape of an archwire passing through the bracket slots in the target situation, and calculating the optimal shape of bends that connect the bracket slots together. The positions of the straight sections and the bends are fed as an input file to a wire bending robot. The wire bending robot need only know the wire size, the shape and size of the slots, and the positions of the slots in the target situation. From this information, robot commands are generated to bend the archwire into the desired shape.

The bracket placement tray is separately manufactured using stereolithography or other similar technique. The treatment planning software generates items 1) and 2) above, and superimposes the brackets on the teeth to generate a three-dimensional model comprising the three-dimensional tooth objects plus the virtual brackets at their intended locations in the observed stage or malocclusion. This three-dimensional model is supplied to a stereolithography (SLA) instrument. The SLA instrument manufactures a plastic model of the teeth with the brackets superimposed on the teeth. A thermoplastic foil is placed above the SLA model and the model and foil are placed within a pressure chamber. The chamber is pressurized so that the foil envelops the dentition and the brackets. After cooling, the foil is removed from the model. The foil, now in the shape of a transfer tray, has small indentations where the brackets are located. Real brackets are placed in these indentations. The orthodontist uses indirect bonding techniques to bond the brackets to the teeth. The transfer tray positions the brackets on the teeth at the desired location. After the bonding is complete, the orthodontist removes the transfer tray, resulting in the brackets bonded to the teeth at the desired location. A further scan of the dentition can be made at this step to verify the position of the brackets. Any substantial deviation in the bracket position can be accounted for by modification of the archwire, again using the treatment planning features described above.

There will always be some small gap between the bracket base (the part bonded to the tooth) and the tooth, as an off-the-shelf bracket will never precisely match the individual tooth of any given patient. One option is to fill the gap using a surplus of bonding adhesive during bonding. Another option is to equip the base of the bracket with a customized pad made from an adhesive.

Customized bracket pads can be manufactured using a variety of techniques. One possibility is to bond a blob of adhesive to a bracket base, and mill the blob using a milling machine to match the tooth surface. Since the tooth surface is known precisely from the scanning, and the position of the bracket base relative to the surface is also known precisely, a very accurate bracket pad can be manufactured in this fashion. Another technique is to stamp out a bracket pad using stamping machine either in the desired shape or as a blank and milling the stamped pad to the desired shape. A third possibility is creating a negative of the customized pad, forming the pad in a mold, bonding the pad to the bracket and the orthodontist trimming the pad as necessary when the pad is bonded to the tooth.

Once the brackets have been bonded to the teeth, a scan of the bracket placement is made. The scan is compared to the digital template of the expected bracket position. If the bracket is placed incorrectly, the bracket can be re-bonded to the tooth. Alternatively, corrections to the wire may be made if necessary to account for displacement of the brackets from their expected position. Basically, this is done by simulating the position of the teeth with the actual bracket placement at the target situation and correcting the shape of the archwire as necessary, or obtaining a new archwire based on the actual placement of the brackets.

It is also possible to manufacture a transfer tray without the intermediate step of a positive SLA model representing the dentition and the brackets. These trays may be either similar to the plastic sheets and just be fabricated using rapid prototyping methods (SLA, laser sintering, milling, 3-D printing, etc.), or they have more sophisticated geometry including features to hold the brackets and features to provide proper positioning at the dentition. Additionally, bracket placement jigs can be milled from the three-dimensional models of the dentition and the brackets using techniques described in, for example, in the Andreiko patent cited earlier.

As another possibility, the customized bracket bonding pads based on the virtual tooth/bracket geometry can be fabricated. Such bonding pads may include additional material which conforms to the surface of the tooth to act as a placement jig for the tooth to allow the bracket bonding pad to be precisely located on the tooth. Then the bracket is bonded to the bracket bonding pad. The additional material is then removed.

Further details of the appliance manufacturing steps are not particularly relevant to the present discussion. The interested reader is directed to the patent application of Werner Butscher et al., entitled ROBOT AND METHOD FOR BENDING ORTHODONTIC ARCHWIRES AND OTHER MEDICAL DEVICES, Ser. no. 09/834,967 filed Apr. 13, 2001 and in the patent application of Rudger Rubbert et al, also filed Apr. 13, 2001, entitled INTERACTIVE ORTHODONTIC CARE SYSTEM BASED ON INTRA-ORAL SCANNING OF TEETH, Ser. No. 09/835,039, the contents of both of which are incorporated by reference herein.

With the above description in mind, it will be appreciated that he treatment planning functions can be performed with the importation of any 3D object from any source. While the preferred embodiment uses the scanned three-dimensional model from the hand-held scanner, this is not necessary or required. The software preferably has import filter for common types of files of 3D objects including STL, DXF, VRML etc.

Additionally, another key aspect of the treatment planning software is that it permits the placing of brackets onto tooth models in an arbitrary manner and virtually "bonding" those brackets to the teeth so that they move together. While the present embodiment has described a landmarking feature by which the user places landmarks on the teeth and the brackets are placed on the landmarks, this may be performed in other ways, including automatically with no user involvement based on parameters such as crown height, bracket type, tooth size, etc.

As indicated above, the software also provides for aligning of the brackets along virtual wire of any shape. Thus, as the user changes the shape of the archwire, the brackets follow this shape, thereby indicating tooth position correction in the target situation. This feature allows the user to drive the treatment planning based on wire shape. Conversely, the wire shape can be dictated by the placement of the brackets on the teeth. Thus, the treatment plan can be one driven by bracket placement. Obviously, wide variety is possible in the shape and design of the wire.

Furthermore, by providing for the simulation of teeth in both maxilla and mandible together, the software provides for a wide variety in defining the maxillary/mandible relationship, the occlusal plane and the mid-line of the teeth.

Another significant aspect of the software is that it provides for virtually unlimited 3D measuring features using the marking icon and measurement feature described earlier. This feature offers a powerful diagnostic tool, as well as a tool for monitoring the progress of treatment and quantifying results.

Because the teeth are represented as complete three-dimensional virtual objects, it is possible to detect the collision between teeth or between teeth and brackets in the simulation of movement of teeth from the current to the target situation. The point cloud representing tooth objects defines a surface, when surfaces come in contact during the tooth movement a collision is simulated. This collision is detected by suitable collision detection algorithms. When the collisions are detected, the user can be notified of the collision and resolve the conflict between teeth, for example by selecting one tooth as a primary tooth and moving that tooth first in an initial stage of treatment, and then moving the other tooth in a secondary stage of treatment. These features are described in further detail in U.S. Pat. No. 6,250,918 to Sachdeva et al., the contents of which are incorporated by reference herein.

Another advantage of the instant treatment planning software is that it offer the user real time simulation with immediate feedback on the effect of user specified tooth movement. When a value is entered into a field in the display or the user uses the navigation tools, results are displayed immediately. Further the system offers arbitrary access to every object, including election, navigation and export.

From the above discussion, it will be appreciated that while we have described a presently preferred embodiment of a digital treatment planning method and software, wide variation is possible in how the treatment planning is implemented, how appliances are designed, and the features and functionality that may be provided to the user. The true spirit and scope of the invention will be understood by reference to the appended claims.

What is claimed is:

1. Treatment planning apparatus for an orthodontic patient, comprising:
   a workstation having a processing unit and a display;
   a memory storing a virtual three-dimensional model of teeth and/or associated anatomical structures representing the dentition of a patient;
   software executable by said processing unit to access said model and display said model on said display;
   said software further including navigation tools enabling a user to interactively manipulate said model on said display and simulate the movement of at least one tooth in said model relative to other teeth in said model to arrive at a target situation for said dentition;
   a library of virtual, three-dimensional orthodontic brackets, said software permitting a user to access said virtual brackets, place said virtual brackets on said virtual model of the dentition of the patient at user specified, arbitrary positions, and simultaneously display both said virtual brackets and said virtual model;
   and wherein the shape and configuration of a customized archwire for straightening teeth is automatically determined by said software as a consequence and result of the placement location of said brackets on said teeth and said target situation for said dentition.

2. The apparatus of claim 1, further comprising:
   a library of virtual, three-dimensional orthodontic brackets, said software permitting a user to access said virtual brackets, place said virtual brackets on said virtual model of the dentition of the patient, and simultaneously display both said virtual brackets and said virtual model.

3. The apparatus of claim 2, wherein said software displays an independent virtual three-dimensional object representing an orthodontic archwire, said archwire and orthodontic brackets representing a prospective appliance for treatment for said patient to move the patient's teeth to a target situation.

4. The apparatus of claim 1, wherein said virtual model comprises a set of virtual, individual three-dimensional tooth objects and wherein said software enables a user of said workstation to select an archform for said virtual model, wherein said set of tooth objects are moved with respect to said archform.

5. The apparatus of claim 1, wherein said virtual model comprises a set of virtual, individual three-dimensional tooth objects and wherein said set of tooth objects are moved with respect to each other to define an archform representing, at least in part, a proposed treatment for the patient.

6. The apparatus of claim 4 or claim 5, wherein said software displays a screen permitting a user to modify the position of said individual tooth objects with respect to said at least one of the following: said archform, associated anatomical structures, and other teeth.

7. The apparatus of claim 4 or claim 5, wherein said software displays a screen permitting a user to customize the shape of said archform.

8. The apparatus of claim 1, wherein said virtual model of teeth comprises a set of virtual, individual three-dimensional tooth objects and wherein individual ones of said virtual tooth objects can be individually selected and moved relative to other teeth in said set of virtual tooth objects.

9. The apparatus of one of claims 4,5,8, wherein said virtual tooth objects are obtained by software comparing said virtual model of teeth with a set of virtual three-dimensional template teeth.

10. The apparatus of one of claims 4,5,8, further comprising a second computer remotely located from said workstation, wherein said virtual tooth objects are obtained by software comparing said virtual model of teeth with a set of virtual three-dimensional template teeth, and wherein said software performing said comparing is performed by said second computer.

11. The apparatus of claim 1, wherein said software simulates the movement of teeth from an observed, present situation of said dentition to a target situation for said dentition reflecting a prospective treatment of said patient.

12. The apparatus of claim 1, further comprising:
a scanning system for scanning of the dentition of the patient or a model of the dentition, said scanning system further comprising software for processing captured images from said scanning system and converting said captured images into said virtual model of the dentition.

13. The apparatus of claim 12, wherein said scanning system further comprises a hand-held scanner adapted for intra-oral, in-vivo scanning of a human patient.

14. The apparatus of claim 1, wherein the virtual model of the dentition includes upper and lower archforms representing the teeth of the upper and lower arches of the patient, and wherein the software enables a user to simulate changes in the placement of the upper archform relative to the lower archform.

15. The apparatus of claim 1, said software further including a measurement tool enabling a user to measure in three planes of space the distance between two points on said virtual three dimensional model.

16. The apparatus of claim 1, said software further comprising a zoom feature enabling a user to change the size of a tooth in the virtual model of the dentition.

17. The apparatus of claim 1, wherein the target situation comprises an intermediate target position representing a position of the teeth between a malocclused position and an ideal tooth position.

18. A method of digital treatment planning for an orthodontic patient on a workstation having a processing unit, a user interface including a display and software executable by said processing unit, comprising the steps of:
obtaining and storing a three-dimensional virtual model of teeth representing the dentition of the patient in a current situation;
displaying the virtual model on the display;
moving the position of teeth in the virtual model relative to each other so as to place the teeth of the virtual model into a target situation;
displaying the virtual model with the teeth moved to the target situation;
placing virtual brackets on said virtual model; and
automatically obtaining three-dimensional shape parameters for a customized orthodontic archwire to move the patient's teeth from the current situation to the target situation from the placement of the brackets on the virtual model and the placement of the teeth in the target situation.

19. The method of claim 18, wherein said orthodontic appliance comprises an archwire.

20. The method of claim 18, wherein the orthodontic appliance comprises a retainer.

21. The method of claim 18, wherein said orthodontic appliance comprises a removable orthodontic appliance.

22. The method of claim 18, further comprising the step of determining whether a collision of teeth occurs during the movement of the virtual model of the teeth from the current situation to the target situation.

23. The method of claim 18, further comprising the step of exporting the parameters for the orthodontic appliance to an appliance manufacturing facility and manufacturing the appliance from the exported parameters.

24. The method of claim 23, wherein said orthodontic appliance comprises an archwire.

25. The method of claim 23, wherein said orthodontic appliance comprises a removable orthodontic appliance.

26. The method of claim 18, further comprising the step of providing navigational tools on said display enabling a user to view said virtual model in either the target or the current situation in a cross-sectional clipping plane.

27. The method of claim 26, further comprising the step of providing a screen display enabling a user to select a desired archform for said virtual model.

28. The method of claim 27, wherein said screen display enables a user to change the shape of said arch form.

29. The method of claim 18, further comprising providing a measuring tool for measuring said virtual model.

30. The method of claim 18, further comprising the step of providing screen displays on said display enabling a user of the workstation to operate the user interface so as to place virtual three-dimensional objects representing an orthodontic appliance onto the surface of teeth in said virtual model.

31. The method of claim 30, further comprising the step of providing screen displays on said display enabling a user to change the position of said orthodontic appliance relative to said teeth.

32. The method of claim 30, wherein said orthodontic appliances comprises brackets and an archwire, and wherein the method further comprises the step of displaying on the display a virtual three-dimensional object representing said archwire, said archwire passing through slots of said brackets.

33. The method of claim 30, wherein the orthodontic appliance comprises a set of brackets, location information for said brackets releative to teeth in said virtual model, and an archwire.

34. The method of claim 18, wherein the target situation comprises an intermediate target position representing a position of the teeth between a malocclused position and an ideal tooth position.

35. The method of claim 18, further comprising the step of scanning the dentition of the patient during the course of treatment and comparing the progress of tooth movement during the course of treatment with the target situation.

36. An orthodontic workstation, comprising:
a processing unit and a display;
a memory storing a virtual three-dimensional model of teeth representing a desired target situation for the dentition of a patient; and
software executable by said processing unit to access said model and display said model on said display;
and wherein said workstation receives data representing a three-dimensional scan of the patient's dentition having brackets placed on the surface of the teeth of the patient, and wherein said software automatically derives the three-dimensional configuration of a customized orthodontic archwire to move the teeth to the desired target situation, based on the location of brackets as actually placed on the surface of the teeth and the desired target situation for the teeth of the patient.

37. The workstation of claim 36, wherein said memory stores both a virtual three-dimensional model of the teeth and/or associated anatomical structures representing the dentition of a patient and a virtual three-dimensional model of a desired target situation for the patient.

38. The workstation of claim 36, wherein said memory further stores a virtual bracket template comprising a virtual three-dimensional model of a set of brackets as placed on the surface of the virtual three-dimensional model of the teeth and/or associated anatomical structures representing the dentition of a patient.

39. The workstation of claim 38, wherein said workstation receives data representing a scan of a patient having brackets placed on the surface of the teeth of the patient, and wherein said software enables a user to compare the location of brackets as placed on the surface of the teeth with said virtual bracket template and quantify differences between the actual placement and the virtual bracket template.

40. The workstation of claim 38, wherein said memory further stores an archwire template comprising a virtual three-dimensional model of an orthodontic archwire as placed on the surface of the virtual three-dimensional model of the teeth and/or associated anatomical structures representing the dentition of a patient.

41. The workstation of claim 4, wherein said workstation receives data representing a scan of a patient having an archwire placed on brackets bonded to the surface of the teeth of the patient, and wherein said software enables a user to compare the location of said archwire as actually places on the surface of the teeth with said archwire template and quantify differences between the actual placement and the archwire template.

42. The apparatus of claim 36, wherein the desired target situation comprises an intermediate target position representing a position of the teeth between a malocclused position and an ideal tooth position.

43. A method of digital treatment planning for an orthodontic patient, the patient having orthodontic brackets placed on the teeth of the patient, comprising the steps of:
scanning the patient's dentition, including said brackets, with a scanner to obtain scan data;
converting the scan data to a three-dimensional virtual model of the dentition including the placement of the brackets on the teeth;
obtaining a virtual model of the position of the patient's teeth in a target situation; and
automatically deriving the three-dimensional configuration of a customized orthodontic archwire to move the teeth to the target situation, based on the location of said brackets on said dentition and the target situation for the teeth of the patient.

44. The method of claim 43, wherein the target situation comprises an intermediate target position representing a position of the teeth between an malocclused position and an ideal tooth position.

45. The method of claim 43, further comprising the step of scanning the dentition of the patient during the course of treatment and comparing the progress of tooth movement during the course of treatment with the target situation.

* * * * *